(12) United States Patent
Vogel

(10) Patent No.: US 11,955,229 B2
(45) Date of Patent: Apr. 9, 2024

(54) HEALTH MANAGEMENT PLATFORM

(71) Applicant: Concorde Health, Inc., Boston, MA (US)

(72) Inventor: Jeffrey Vogel, Boston, MA (US)

(73) Assignee: Concorde Health, Inc., Boston, MA (US)

( * ) Notice: Subject to any disclaimer, the term of this patent is extended or adjusted under 35 U.S.C. 154(b) by 352 days.

(21) Appl. No.: 17/293,624

(22) PCT Filed: Nov. 13, 2019

(86) PCT No.: PCT/US2019/061168
§ 371 (c)(1),
(2) Date: May 13, 2021

(87) PCT Pub. No.: WO2020/102345
PCT Pub. Date: May 22, 2020

(65) Prior Publication Data
US 2022/0013217 A1    Jan. 13, 2022

Related U.S. Application Data

(60) Provisional application No. 62/760,295, filed on Nov. 13, 2018.

(51) Int. Cl.
*G16H 40/20* (2018.01)
*G16H 20/30* (2018.01)
(Continued)

(52) U.S. Cl.
CPC .............. *G16H 40/20* (2018.01); *G16H 20/30* (2018.01); *G16H 50/30* (2018.01); *G16H 80/00* (2018.01)

(58) Field of Classification Search
None
See application file for complete search history.

(56) References Cited

U.S. PATENT DOCUMENTS

| | | | |
|---|---|---|---|
| 6,461,162 B1 * | 10/2002 | Reitman | G06Q 10/10 |
| | | | 434/257 |
| 2006/0271407 A1 * | 11/2006 | Rosenfeld | G16H 50/20 |
| | | | 434/262 |

(Continued)

FOREIGN PATENT DOCUMENTS

| | | |
|---|---|---|
| EP | 3355061 A1 | 8/2018 |
| WO | 2006/069342 A2 | 6/2006 |

(Continued)

OTHER PUBLICATIONS

Extended European Search Report issued in European Application No. 19883638.9, dated Jun. 28, 2022, 1 pages.

(Continued)

*Primary Examiner* — John F Mortell
(74) *Attorney, Agent, or Firm* — Brown Rudnick LLP; Adam M. Schoen

(57) ABSTRACT

The invention relates a cloud-based health management platform providing personal injury recovery and/or injury prevention plans tailored to individuals. The platform further allows employers and/or care providers associated with such individuals to maintain continuous engagement therewith, either by way of a fully-automated, or semi-automated, or fully personalized communication with the individuals, to ensure that personal attention is provided for any given individual as needed and further adjusting the plans as required, resulting in improved participation and completion of an individuals recovery and/or prevention plan.

20 Claims, 25 Drawing Sheets

(51) Int. Cl.
*G16H 50/30* (2018.01)
*G16H 80/00* (2018.01)

(56) References Cited

U.S. PATENT DOCUMENTS

| | | | | |
|---|---|---|---|---|
| 2015/0039343 A1* | 2/2015 | Cline | ............... | G16H 10/60 |
| | | | | 705/3 |
| 2015/0040685 A1* | 2/2015 | Nicholson | ............ | A61B 5/4064 |
| | | | | 73/862.51 |
| 2018/0321225 A1* | 11/2018 | Zayed | ............... | G01N 33/573 |
| 2019/0095808 A1* | 3/2019 | Chattopadhyay | .. | G06Q 10/0635 |
| 2019/0343429 A1* | 11/2019 | Elhawary | ............. | A61B 5/6823 |

FOREIGN PATENT DOCUMENTS

| | | |
|---|---|---|
| WO | 2016/201212 A1 | 12/2016 |
| WO | 2018/127372 A1 | 7/2018 |

OTHER PUBLICATIONS

International Search Report and Written Opinion issued in International Application No. PCT/US2019/061168, dated Apr. 2, 2020, 9 pages.

* cited by examiner

FIG. 8A  FIG. 8B  FIG. 8C  FIG. 8D

HEALTH MANAGEMENT PLATFORM

CROSS-REFERENCE TO RELATED APPLICATION(S)

This application is a national stage entry of PCT/US2019/061168 with an International Filing Date of Nov. 13, 2019, which claims priority to, and the benefit of, U.S. Provisional Application No. 62/760,295, filed Nov. 13, 2018, the contents of each of which are incorporated by reference herein in their entireties.

FIELD OF THE INVENTION

The invention relates to systems and methods for providing health management services, and, more particularly, to a cloud-based health management platform for facilitating an injury recovery and/or injury prevention plan for a user and further facilitating the user's compliance with the injury recovery and/or injury prevention plan.

BACKGROUND

Millions of people incur or develop physical injuries or ailments every year, many seeking medical attention to recover from such injuries and ailments. While some people are injured as a result of participating in athletic activities (e.g., professional, amateur, and recreational athletics), many individuals suffer injuries in the workplace, which can be very expensive for an employer or payer. The costs associated with an employee absence incurred by employers and payers include both direct and indirect costs, and are directly correlated with the profitability of the employer. The direct costs include items such as insurance premiums, medical expenses, legal expenses, sick pay, disability income and administrative fees, while the indirect costs include items such as lost productivity, overtime, replacement worker expenses, investigation expenses and decreased product quality. The costs associated with employee absences continue to escalate, and are estimated to exceed $1 trillion per year in the United States alone.

To improve profitability, employers have traditionally opted to focus the majority of their efforts on improving functions or departments that generate revenues, often devoting little or no attention to the practice of health management. However, given the increasingly negative effect that employee health costs are having on the bottom line of many employers, greater efforts are now being directed to proactively managing employee injuries and ailments to reduce the costs associated therewith.

Although many employers now realize the strategic importance of managing workplace injuries, the effective implementation of such management has been relatively difficult. As currently practiced by many employers, workplace injury management is a very fragmented, regulatory laden, form-burdened, manual process that involves a number of different entities. Such entities can include, for example, a case manager, human resource personnel, physicians, physical therapists, occupational therapists, attorneys, insurance carriers, third-party administrators, and governmental personnel. Workplace injury management can require both extensive internal (e.g., department to department, employer to employee) and external (e.g., employer to physician, employer to attorney) communications, and each entity involved in the process can generate a great deal of information that collectively comprise the content of a particular case.

Recent advances in telemedicine, however, have promoted the use of online portals and mobile applications with promise to improve completion rates of injury recovery plans. While certain rehabilitation applications have been implemented, with an aim to improve patient adherence and proper application of at home therapy, such applications still have common drawbacks. For example, current injury recovery systems rely on delivering simple plans to injured individuals, which puts the onus on the individual to stay motivated and on track, ultimately leading to lower recovery rates. In particular, injured workers face a multitude of challenges, from pain control and an understanding of "what should I expect in my recovery course (expectation management)", to anxiety, and communication challenges with employers. Current systems do not address the various issues that an injured worker faces and instead simply focus on treating the physical aspect of the injury, as opposed to the psychosocial aspects. In particular, studies suggest that improved return-to-work rates rely on treating the aspects of recovery that do not explicitly focus on the physical rehabilitation, highlighting the importance of managing the person as a whole. However, current systems lack any real structured means to harness this type of injury recovery and management. Current systems lack personalization to ensure that the employee is receiving the specific care and involvement from the employer and care providers that they require, thereby resulting in lower recovery rates and extended absences from work, subsequently increasing the overall costs for the employer.

SUMMARY

The present invention recognizes the drawbacks of current health service systems, particularly within the workplace environment, and provides a cloud-based health management platform to address such drawbacks.

Aspects of the invention may be accomplished by using a health management platform providing at least a first web portal or user interface (UI) with which an employee patient may interact via an associated computing device, such as a smartphone or tablet or PC. The platform is configured to initially assess and stratify the employee into one of a plurality of risk groups based on specific data provided by the employee, such as the specific details about the injury and personal details about the employee. Each risk group is associated with a respective level of guidance and care provider involvement estimated to be necessary in order to facilitate the employee's compliance with an injury recovery and/or injury prevention plan. In turn, the platform generates and provides a personal injury recovery and/or injury prevention plan tailored to the employee based on the risk group in which the employee has been placed and the specific data provided by the employee. The injury recovery and/or injury prevention plan includes a physical recovery component and a psychosocial health component that is tailored to a risk group into which the employee is initially placed. The platform further includes at least a second web portal or UI with which an employer or care provider associated with the employee may interact, via an associated computing device, so as to monitor the employee's progress and participation with the plan.

The platform provides a suite of features to keep both the employee and the employer and/or care providers in continuous contact and engaged with one another, thereby providing the employee with the feeling of support in their recovery process, as opposed to simply providing recovery exercises and treatments and expecting the employee to complete the plans. For example, the platform further allows allow employers and/or care providers to maintain continuous engagement with the employee, either by way of fully-automated, or semi-automated, or fully personalized communications to ensure that personal attention is provided to the employee as needed, such as answering any questions the employee may have, as well as following up with the employee to see how they are feeling, physically and/or mentally. The platform also allows for the scheduling of events included in the injury recovery and/or injury prevention plan, such as appointments/consultations with care providers, specific physical treatments or exercises, and the like, and further provides reminders/alerts to the employee of such events so as to keep the employee on track. The platform further allows for the employer and/or care provider to modify the plan as needed.

Accordingly, the health management platform of the present disclosure addresses the drawbacks of current health service systems, namely the lack of personalization in current systems. In particular, the health management platform of the present disclosure delivers focused, customized, engaging, and relevant content through continuous engagement between the employee and the employer and/or care providers. The cloud-based platform is conveniently designed such that an employee is able to interact with their injury recovery and/or injury prevention plan via their mobile device, such as their smartphone, requiring very little time and effort. This similarly benefits the employer and care providers. Accordingly, such a system is not overwhelming for employees, yet focused on building healthy behaviors and ultimately improving participation with any given plan and recovery from injuries and/or further preventing injuries. The health management platform of the present invention allows for a team (i.e., employer, insurer, care providers, etc.) to effectively manage communications with the employee and track progress, wherein such a combination of communication and engagement helps employees/patients feel better supported and connected to their employers, which are key qualities in driving better recovery rates. In particular, the system of the present invention focuses on both the physical and psychosocial aspects of recovery, specifically focusing on the psychosocial aspects independent from physical aspects and is configured to establish a coherent relationship therebetween, improving the overall outcome for injury recovery and prevention. In particular, recent literature suggests a system consistent with the present disclosure may result in a 40% improvement in recovery and return-to work rates, which may equate to about 35-45% direct cost savings among those at high risk for longer-term disability.

Certain aspects of the invention relate to a system for providing health management services. The system includes a computer server configured to receive, from a first user, first user data associated with an injury of the first user and stratify, based on the first user data, the first user into one of a plurality of risk groups, wherein each risk group associated with a respective level of guidance and care provider involvement in order to facilitate the first user's compliance with an injury recovery and/or injury prevention plan. The computer server is further configured to generate the injury recovery and/or injury prevention plan tailored to the first user based, at least in part, on which risk group the first user has been placed. The injury recovery and/or injury prevention plan comprises a physical recovery component and a psychosocial health component that is tailored to the risk group into which the first user has been placed, wherein the plan is accessible to the first user via a first portal provided on a cloud-based platform.

In some embodiments, the psychosocial component of the injury recovery and/or injury prevention plan comprises transmission of one or more communication messages to the first user. The risk groups may comprise a first risk group associated with a low level of guidance and care provider involvement, a second risk group associated with a medium level of guidance and care provider involvement greater than the low level, and a third risk group associated with a high level of guidance and care provider involvement greater than the medium level. It should be noted, however, that in other embodiments, the number of risk groups may be more or less. The computer server is configured to transmit the one or more communication messages to the first user based, at least in part, on the level of guidance and care provider involvement associated with the risk group in which the first user has been placed. In some embodiments, at the low level of guidance and care provider involvement, the communication messages comprise automated, chatbot-based communications, at the medium level of guidance and care provider involvement, the communication messages comprise a combination of automated, chatbot-based communications and personal, human-based communications, and at the high level of guidance and care provider involvement, the communication messages comprise personal, human-based communications.

In some embodiments, tailoring of the injury recovery and/or injury prevention plan to the first user comprises automatically predicting, based on real-time analysis of the first user data and risk group data, a level of care to be associated with the plan and types of content to be provided to the first user as part of the physical recovery and psychosocial health components of the plan. In some embodiments, the first user data comprises at least one of injury data, personal data associated with the first user, and preference data associated with the first user's preferred level of guidance for injury recovery and/or injury prevention.

The injury data may comprise information associated with the injury, the information including, but not limited to, location of the injury on the first user's body, symptoms of injury, self-reported pain scale value associated with injury, limitations in function associated with injury, date of injury occurrence, and activity performed by first user at the time of injury occurrence. The personal data may comprise traits and characteristics of the first user selected from the group consisting of: name; date of birth, height, weight, gender, medical history, comorbidity, and smoking status. The preference data may comprise at least one of a self-reported preferred level of guidance and/or care provider involvement related the injury recovery and/or injury prevention plan and self-reported level of experience with injury recovery and/or injury prevention.

In some embodiments, the physical recovery and psychosocial health components of the injury recovery and/or injury prevention plan includes, but is not limited to, one or more suggested consultations with a care provider, one or more suggested injury recovery and/or injury prevention treatments, and one or more communication messages to be transmitted to the first user. The one or more suggested injury recovery and/or injury prevention treatments may comprise physical exercises. The one more communication messages may comprise questions concerning at least one of the first user's current physical health status, the first user's current psychosocial health status, and the first user's participation with the injury recovery and/or injury prevention plan.

The computer server may be configured to monitor the first user's participation and engagement with the injury recovery and/or injury prevention plan based, at least in part, on the first user's interaction with at least one of the physical recovery and psychosocial health components. In particular, the computer server may be configured to receive feedback indicating whether the first user has attended the one or more suggested consultations with the care provider and/or whether the first user has started and/or completed the one or more suggested injury recovery and/or injury prevention treatments. Additionally, or alternatively, the computer server may be configured to receive one or more responses from the first user to one or more communication messages transmitted to the first user.

The computer server may be configured to adjust the injury recovery and/or injury prevention plan based on real-time analysis of the first user's feedback and/or the one or more responses from the first user. Adjustments to the injury recovery and/or injury prevention plan may include one or more adjustments to the physical recovery component and/or psychosocial component including, but not limited to, adjusting frequency of the one or more initially suggested consultations with a care provider, updating the plan to include one or more additional suggested consultations with one or more additional care providers, updating the plan to include one or more additional suggested injury recovery and/or injury prevention treatments, updating the plan to remove the one or more initially suggested injury recovery and/or injury prevention treatments, adjusting frequency of the one or more communication messages to be transmitted to the first user, and adjusting the content of the one or more communication messages to be transmitted to the first user. The computer server may be configured to re-stratify the first user into one of the plurality of risk groups based on real-time analysis of the first user's feedback and/or the one or more responses from the first user.

In some embodiments, the computer server may be configured to track participation and engagement data related to the first user's participation and engagement with the injury recovery and/or injury prevention plan, wherein tracking participation and engagement data includes aggregating and storing the participation and engagement data in a database. In some embodiments, the participation and engagement data is accessible to at least the first user via the first portal provided on the cloud-based platform and further accessible to at least an authorized second user via a second portal provided on the cloud-based platform. The computer server is configured to communicate and exchange data, over a network, with a first computing device associated with the first user and a second computing device associated with the second user. The first portal provides an interface on the first computing device with which the first user can interact and the second portal provides and interface on the second computing device with which the second user can interact for the management of the first user's injury recovery and/or injury prevention plan and/or monitoring of the first user's participation and engagement with the injury recovery and/or injury prevention plan.

In some embodiments, the first user may include an employee of a company and the second user may include, but is not limited to, an administrative staff member of the company, a management member of the company, and a care provider for providing physical and/or psychosocial care to the first user. The care provider may include, but is not limited to a physician, physician assistant, psychologist, psychiatrist, physical therapist, occupational therapist, social worker, therapist, counselor, and life coach.

In some embodiments, the system of the present disclosure further includes a plurality of databases. For example, in one embodiment, the system includes a user database for storing profiles associated with at least the first user and the second user, wherein the first user profile comprises the first user data associated with an injury of the first user. The system may include a plan database for storing at least the injury recovery and/or injury prevention plan generated for and tailored to the first user. The system may include a consultation scheduling database for storing one or more consultations with one or more care providers. The system may include a treatment database for storing media comprising injury recovery and/or injury prevention treatments, the media comprising an image file, a video file, an audio file, a document file, and a combination thereof. The system may include a communication message database for storing incoming and outgoing messages received from or delivered to the first user. The system may include a participation/engagement database for storing participation and engagement data related to the first user's participation and engagement with the injury recovery and/or injury prevention plan.

In some embodiments, the computer server is configured to restrict access to data associated with the first user based, at least in part, on a level of authority associated with the second user requesting access to the data. For example, upon receiving a request from the second user for access to any data associated with the first user, the server may be configured to compare request data with one or more authorized user profiles to determine a level of access to data associated with the first user for the second user associated with the request and, upon a positive correlation of the request data with an authorized profile, the computer server is configured to grant the second user access to the data associated with the first user.

DETAILED DESCRIPTION

Figure 1:
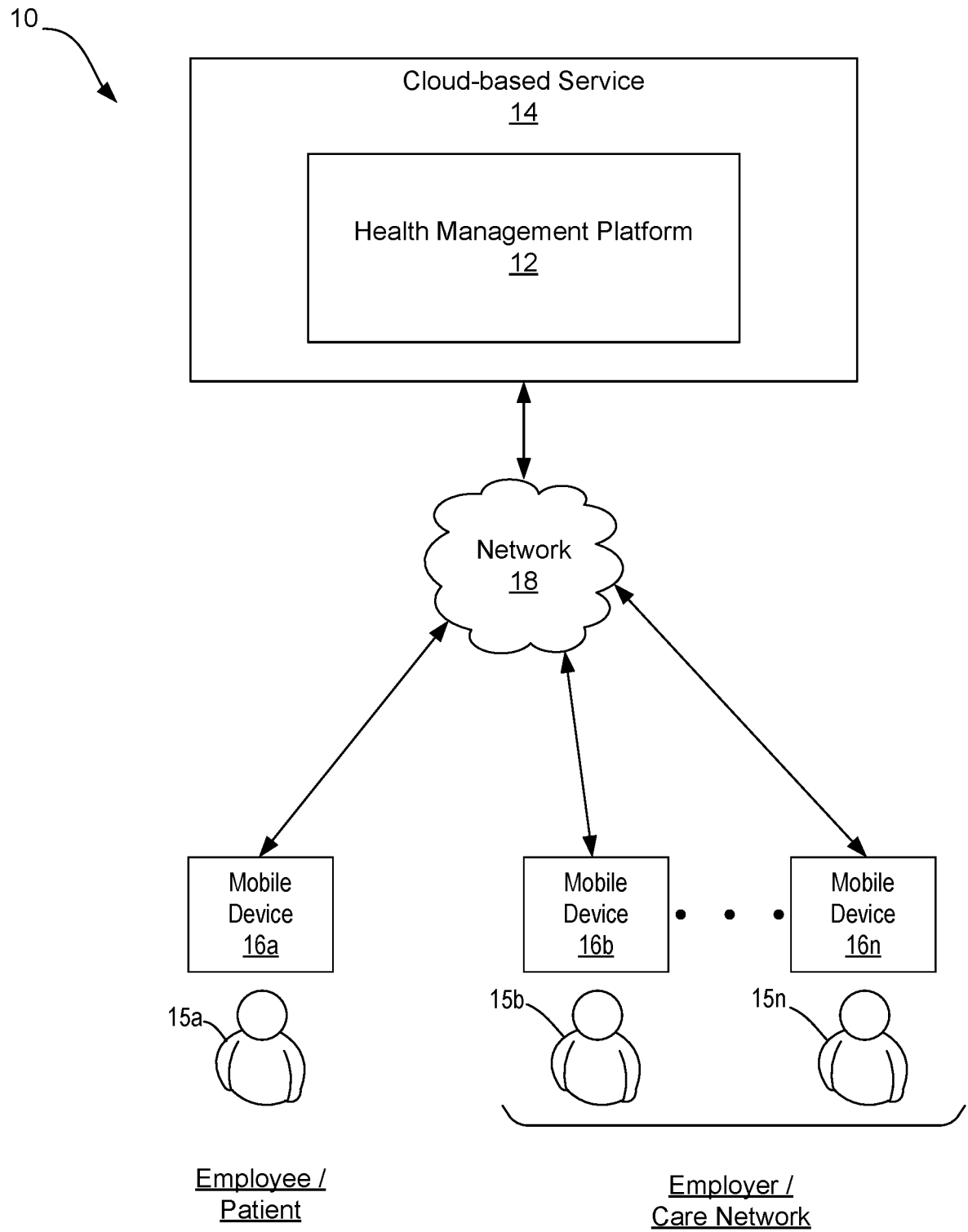
FIG. 1 is a block diagram illustrating one embodiment of an exemplary system for providing a health management services.

The present invention is directed to a cloud-based health management platform providing personal injury recovery and/or injury prevention plans tailored to individuals. The health management platform provides at least a first web portal or user interface (UI) with which an employee, or patient, for example, may interact via an associated computing device, such as a smartphone or tablet or PC. The platform is configured to initially assess and stratify the employee into one of a plurality of risk groups based on specific data provided by the employee, such as the specific details about the injury and personal details about the employee. Each risk group is associated with a respective level of guidance and care provider involvement estimated to be necessary in order to facilitate the employee's compliance with an injury recovery and/or injury prevention plan. In turn, the platform generates and provides a personal injury recovery and/or injury prevention plan tailored to the employee based on the risk group in which the employee has been placed and the specific data provided by the employee. The injury recovery and/or injury prevention plan includes a physical recovery component and a psychosocial health component that is tailored to a risk group into which the employee is initially placed. The platform further includes at least a second web portal or UI with which an employer or care provider associated with the employee may interact, via an associated computing device, so as to monitor the employee's progress and participation with the plan.

The platform provides a suite of features to keep both the employee and the employer and/or care providers in continuous contact and engaged with one another, thereby providing the employee with the feeling of support in their recovery process, as opposed to simply providing recovery exercises and treatments and expecting the employee to complete the plans. For example, the platform further allows allow employers and/or care providers to maintain continuous engagement with the employee, either by way of fully-automated, or semi-automated, or fully personalized communications to ensure that personal attention is provided to the employee as needed, such as answering any questions the employee may have, as well as following up with the employee to see how they are feeling, physically and/or mentally. The platform also allows for the scheduling of events included in the injury recovery and/or injury prevention plan, such as appointments/consultations with care providers, specific physical treatments or exercises, and the like, and further provides reminders/alerts to the employee of such events so as to keep the employee on track. The platform further allows for the employer and/or care provider to modify the plan as needed.

Accordingly, the health management platform of the present disclosure addresses the drawbacks of current health service systems, namely the lack of personalization in current systems. In particular, the health management platform of the present disclosure delivers focused, customized, engaging, and relevant content through continuous engagement between the employee and the employer and/or care providers. The cloud-based platform is conveniently designed such that an employee is able to interact with their injury recovery and/or injury prevention plan via their mobile device, such as their smartphone, requiring very little time and effort. This similarly benefits the employer and care providers. Accordingly, such a system is not overwhelming for employees, yet focused on building healthy behaviors and ultimately improving participation with any given plan and recovery from injuries and/or further preventing injuries. The health management platform of the present invention allows for a team (i.e., employer, insurer, care providers, etc.) to effectively manage communications with the employee and track progress, wherein such a combination of communication and engagement helps employees/patients feel better supported and connected to their employers, which are key qualities in driving better recovery rates. It should further be noted that the platform may generally be soft-coded, thereby allowing for a specific client (i.e., an employer, insurer, or care provider) to have the interface customized to their preferences.

FIG. 1 illustrates one embodiment of an exemplary system 10 consistent with the present disclosure. As shown, system 10 includes a health management platform 12 embodied on an internet-based computing system/service. For example, as shown, the health management platform 12 may be embodied on a cloud-based service 14, for example. The health management platform 12 is configured to communicate and share data, specifically health-related data, with one or more users 15(1)-15(n) via user mobile devices 16(a)-16(n) over a network 18. In the present context, at least some of the users include employees or patients (i.e., employee 15a), while other users may include one or more members of a company (i.e., employer of the employee 15a) or a care network (users 15b-15n) associated with a given employee. For example, the users associated with the company/employer may include an administrative staff member or management member of the company. The care provider may include, but is not limited to, a physician, physician assistant, psychologist, psychiatrist, physical therapist, occupational therapist, social worker, therapist, counselor, and life coach.

The network 18 may represent, for example, a private or non-private local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). In alternative embodiments, the communication path between the mobile devices 16 and/or between the mobile devices 16 and the cloud-based service 14, may be, in whole or in part, a wired connection.

The network 18 may be any network that carries data. Non-limiting examples of suitable networks that may be used as network 18 include Wi-Fi wireless data communication technology, the internet, private networks, virtual private networks (VPN), public switch telephone networks (PSTN), integrated services digital networks (ISDN), digital subscriber link networks (DSL), various second generation (2G), third generation (3G), fourth generation (4G) cellular-based data communication technologies, Bluetooth radio, Near Field Communication (NFC), the most recently published versions of IEEE 802.11 transmission protocol standards as of October 2018, other networks capable of carrying data, and combinations thereof. In some embodiments, network 18 is chosen from the internet, at least one wireless network, at least one cellular telephone network, and combinations thereof. As such, the network 18 may include any number of additional devices, such as additional computers, routers, and switches, to facilitate communications. In some embodiments, the network 18 may be or include a single network, and in other embodiments the network 18 may be or include a collection of networks.

The health management platform 12 is configured to communicate and share data with the mobile devices 16 associated with one or more users 15. Accordingly, the mobile device 16 may be embodied as any type of device for communicating with the health management platform 12 and cloud-based service 14, and/or other user devices over the network 18. For example, at least one of the user devices may be embodied as, without limitation, a computer, a desktop computer, a personal computer (PC), a tablet computer, a laptop computer, a notebook computer, a mobile computing device, a smart phone, a cellular telephone, a handset, a messaging device, a work station, a distributed computing system, a multiprocessor system, a processor-based system, and/or any other computing device configured to store and access data, and/or to execute software and related applications consistent with the present disclosure. In the embodiments described here, the mobile device 16 is generally embodied as a smartphone or tablet. However, it should be noted that one or more devices 16 may include a computer, a desktop computer, a personal computer (PC), a tablet computer, a laptop computer, a notebook computer, and the like.

As will be described in greater detail herein, the health management platform 12 provides at least a first web portal or user interface (UI) with which an employee (user 15a) may interact via the associated mobile device 16a. The employee (user 15a) may generally be presented with an initial login screen, and, upon entering their credentials, or registering for the first time, the employee can then access and interact with the health management services application, essentially providing direct user input with the health management service offered by the health management platform 12. The employee may provide specific data, such as specific details about the injury and personal details about themselves and the platform, in turn, is configured to provide a personal injury recovery and/or injury prevention plan tailored to that employee based, at least in part, on the specific data that they provided. The platform 12 further includes at least a second web portal or UI with which an employer or care provider (user 15b) associated with the employee may interact, via an associated computing device, so as to monitor the employee's progress and participation with the injury recovery and/or injury prevention plan, engage in communication with the employee, and, in some instances, modify/update the plan, as will be described in greater detail herein.

It should be noted that embodiments of the system 10 of the present disclosure include computer systems, computer operated methods, computer products, systems including computer-readable memory, systems including a processor and a tangible, non-transitory memory configured to communicate with the processor, the tangible, non-transitory memory having stored instructions that, in response to execution by the processor, cause the system to perform steps in accordance with the disclosed principles, systems including non-transitory computer-readable storage medium configured to store instructions that when executed cause a processor to follow a process in accordance with the disclosed principles, etc.

Figure 2:
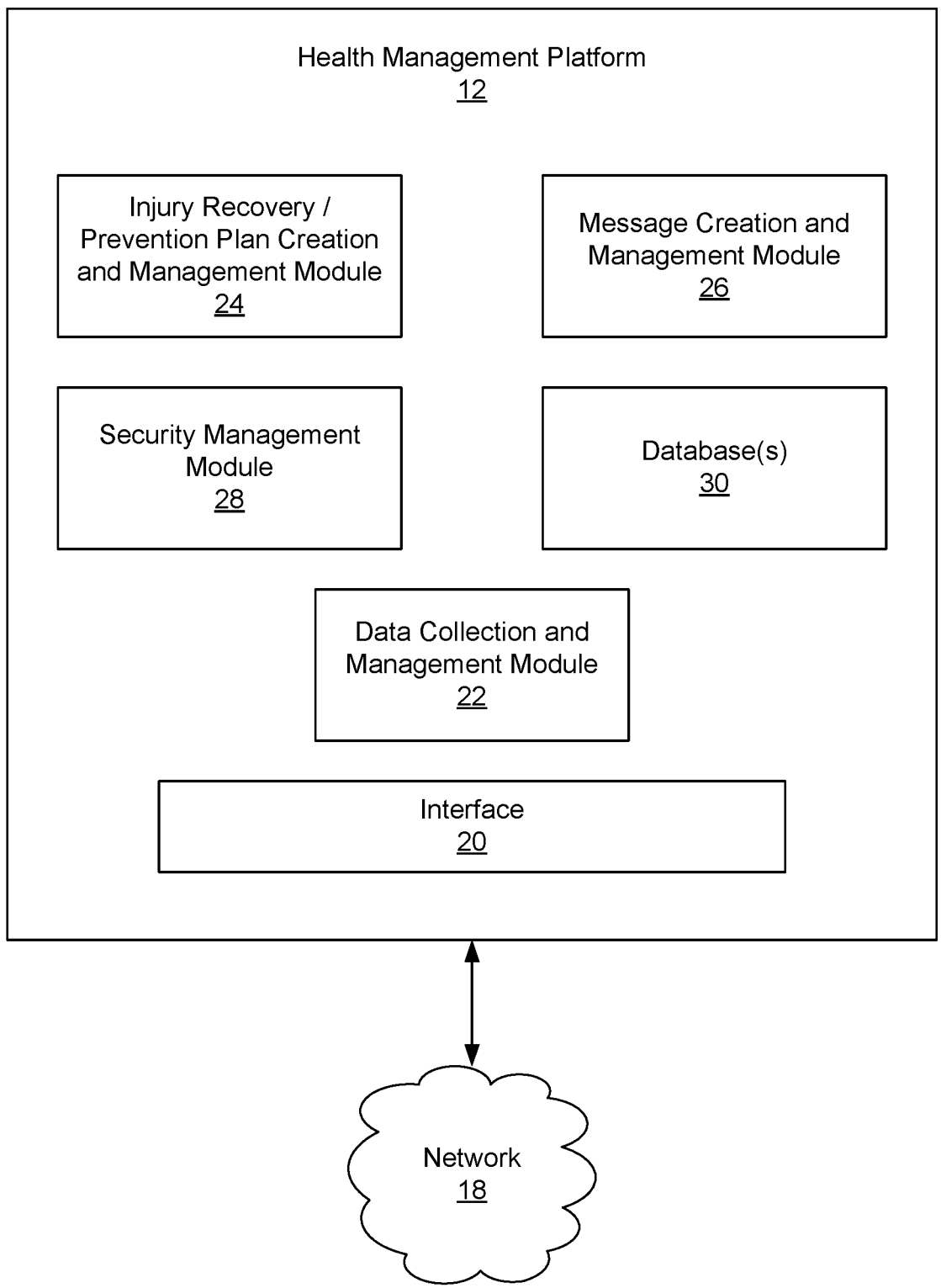
FIG. 2 is a block diagram illustrating the health management platform of FIG. 1 in greater detail.
Figure 3:
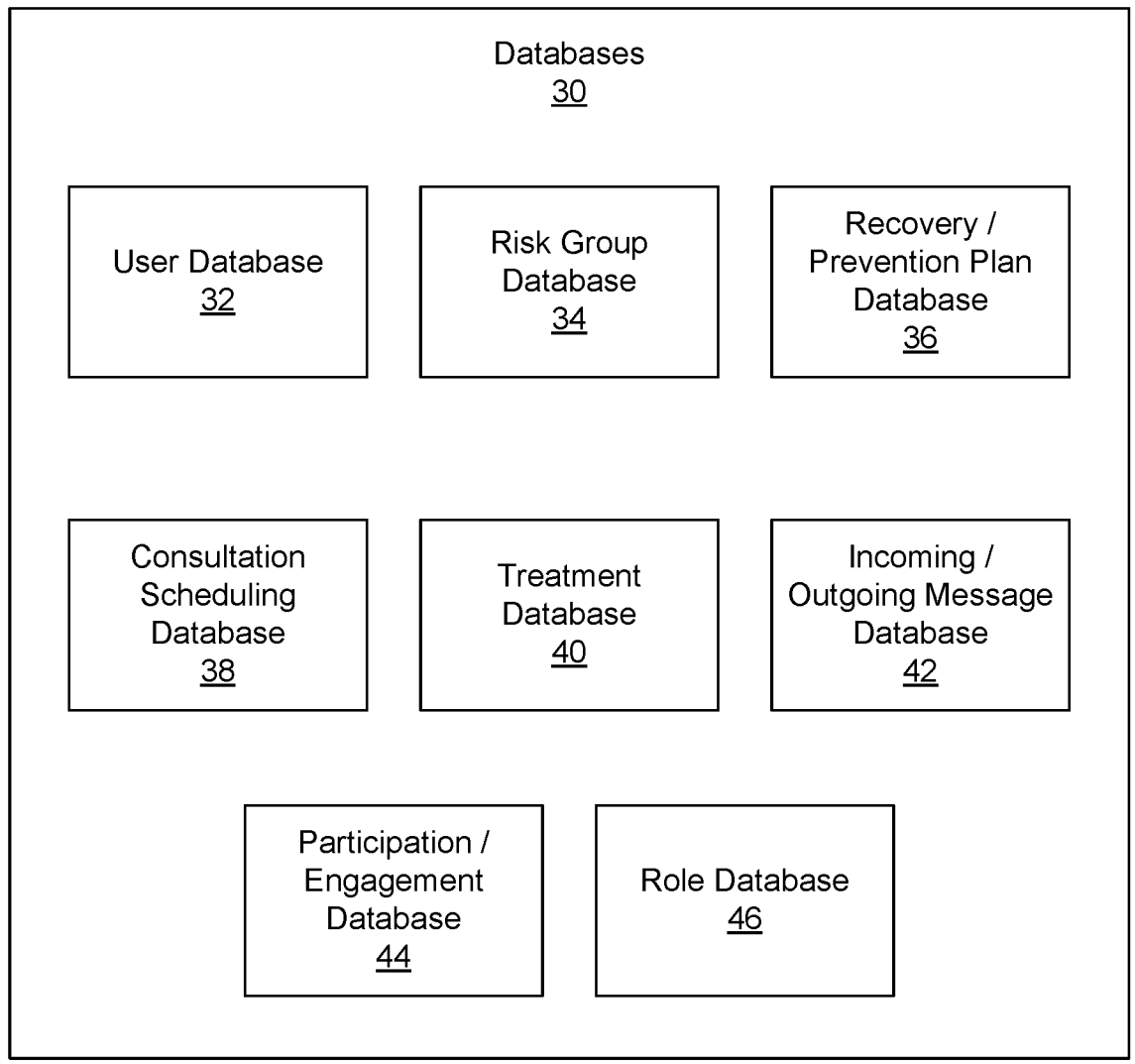
FIG. 3 is a block diagram illustrating the various databases in greater detail.

FIG. 2 is a block diagram illustrating the health management platform 12 of FIG. 1 in greater detail. As shown, the health management platform 12 may include an interface 20, a data collection and management module 22, an injury recovery/prevention plan creation and management module 24, a message creation and management module 26, a security management module 28, and various databases for storage of data, further described with reference to FIG. 3. In particular, the various databases for storage of data include, but are not limited to, a user database 32 for storing profiles associated with at least employees and employers or care providers, a risk group database 34 for storing data related to a plurality of risk groups, a recovery/prevention plan database 36 for storing the injury recovery and/or injury prevention plans generated for and tailored to employees, a consultation scheduling database 38 for storing one or more consultations with one or more care providers, a treatment database 40 for storing media comprising injury recovery and/or injury prevention treatments (i.e., an image file, a video file, an audio file, a document file, and a combination thereof), an incoming/outgoing message database 42 for storing incoming and outgoing messages received from or delivered to the employee, a participation/engagement database 44 for storing participation and engagement data related to the employee participation and engagement with respective injury recovery and/or injury prevention plans, and a role database 46 for storing different group-based roles associated with levels of authorization. The data collection and management module 22 may be configured to communicate and exchange data with each of the databases.

The interface 20 may generally allow a user (e.g., an authorized user) to access data on the health management platform 12, via a mobile software application, for example, provided on a mobile device or via a web-based portal. For example, upon accessing a mobile software application, the interface 20 may be presented to the user via their device 16, in which the user may navigate a dashboard or standard platform interface so as to view data (stored in one or more of the databases), as will be described in greater detail herein. In particular, upon registering or logging, the employee may first provide data associated with specific details about their injury and personal details about themselves. For example, the employee may be presented a set of questions, generally in the form of an evaluation, which prompts them to provide requested information about the injury. For example, such information may include, but is not limited to, a location of the injury on their body, symptoms of injury, self-reported pain scale value associated with injury, limitations in function associated with injury, date of injury occurrence, and activity performed by employee at the time of injury occurrence. The employee may also be prompted to provide personal data, such as traits and characteristics of themselves, including, but not limited to, name, date of birth, height, weight, gender, medical history, comorbidity, smoking, the type of industry they are employed, specific activities that are part of day to day work, the amount of involvement in such activities, history of any injuries to any specific body parts and any residual effects.

The employee may further be prompted to provide preference data, such as, for example, a self-reported preferred level of guidance and/or care provider involvement related the injury recovery and/or injury prevention plan and self-reported level of experience with injury recovery and/or injury prevention. In some embodiments, the employee may be prompted to provide responses to a series of questions used to gauge the user's level of concern over their injury as well as a respective level of guidance and care provider involvement necessary to help the user recover. In particular, the platform 12 may provide a series of questions in which the user is prompted to provide responses in the form of scaled ratings associated with, but not limited to, the length of time the user has been injured, the user's perceived level of pain associated with the injury, the user's perceived level of work that they can perform, the user's perceived level of sleep, the user's perceived level of depression or anxiety, the user's perceived level of risk that the pain may become persistent, and the user's perceived estimation that they will be able to resume work within a certain time period.

Upon receiving the employee data, the injury recovery/prevention plan creation and management module 24 is configured to stratify, based on the employee data, the employee into one of a plurality of risk groups, wherein each risk group associated with a respective level of guidance and care provider involvement in order to facilitate the employee's compliance with an injury recovery and/or injury prevention plan and then generate the injury recovery and/or injury prevention plan tailored to the employee user based, at least in part, on which risk group the employee has been placed. The injury recovery and/or injury prevention plan comprises a physical recovery component and a psychosocial health component that is tailored to the risk group into which the employee has been placed. At this point, the employee is provided their tailored injury recovery and/or injury prevention plan, which accessible to the employee via a first portal provided on the platform 12.

The tailoring of the injury recovery and/or injury prevention plan to the employee comprises automatically predicting, based on real-time analysis of the employee data and risk group data, a level of care to be associated with the plan and types of content to be provided to the employee as part of the physical recovery and psychosocial health components of the plan. For example, the injury recovery/prevention plan creation and management module 24 may include custom, proprietary, known and/or after-developed statistical analysis code (or instruction sets), hardware, and/or firmware that are generally well-defined and operable to receive two or more sets of data and identify, at least to a certain extent, a level of correlation and thereby associate the sets of data with one another based on the level of correlation. As such, the injury recovery/prevention plan creation and management module 24 may analyze data sets from any one of the databases (user database 32, risk group database 34, recovery/prevention plan database 36, consultation scheduling database 38, treatment database 40, and incoming/outgoing message database 42) in order to tailor the injury recovery and/or injury prevention plan to the employee.

The physical recovery and psychosocial health components of the injury recovery and/or injury prevention plan include, but are not limited to, one or more suggested consultations with a care provider, one or more suggested injury recovery and/or injury prevention treatments, and one or more communication messages to be transmitted to the employee. The one or more suggested injury recovery and/or injury prevention treatments may include physical exercises. The one more communication messages may include questions concerning at least one of the employee's current physical health status, the employee's current psychosocial health status, and the employee's participation with the injury recovery and/or injury prevention plan.

The psychosocial component of the injury recovery and/or injury prevention plan may include transmission of one or more communication messages to the employee via the message creation and management module 26. In particular, the risk groups comprise at least a first risk group associated with a low level of guidance and care provider involvement, a second risk group associated with a medium level of guidance and care provider involvement greater than the low level, and a third risk group associated with a high level of guidance and care provider involvement greater than the medium level. It should be noted, however, that in other embodiments, the number of risk groups may be more or less.

As such, the message creation and management module 26 is configured to create and transmit one or more communication messages to the employee based, at least in part, on the level of guidance and care provider involvement associated with the risk group in which the employee has been placed. For example, at the low level of guidance and care provider involvement, the communication messages comprise automated, chatbot-based communications. At the medium level of guidance and care provider involvement, the communication messages comprise a combination of automated, chatbot-based communications and personal, human-based communications. Finally, at the high level of guidance and care provider involvement, the communication messages comprise personal, human-based communications.

It should be noted that in some embodiments, while the user is registering or logging in to the health management service offered by the health management platform 12 (i.e., while the employee provides specific data, such as specific details about the injury and personal details about themselves), the platform is configured to use a multivariable-based backend analysis to identify and deploy specific resources for the user in real-, or near real-, time, even prior to the completion of an onboarding process and thus prior to the generation of a personal injury recovery and/or injury prevention plan. For example, a user may be interacting with the interface during an onboarding process, in which the user if provided basic information, such as personal details about themselves as well as specific details about the injury. The platform is configured to analyze, during the onboarding process, the user data in real-, or near real-, time and identify one or more resources tailored to the user based on the analysis of the user data. The platform is further configured to deploy, during the onboarding process, the one or more identified resources to the user. For example, the deployment of the one or more identified resources may include transmission of one or more communication messages to the user, wherein the one or more communication messages may include an indication that human to human interaction is required, as more details may be required that necessitates the need for human to human interaction. In one embodiment, an invitation may be sent to the user as they are progressing through the onboarding process, wherein the invitation is for an audio and/or video call with a person associated with the user's employer (i.e., an administrative staff member or management member) or with a care provider. In other embodiments, an alert may be sent to the user as they are progressing through the onboarding process, wherein the alert may suggest that the user contact emergency services (i.e., if the user is providing certain injury-related data that correlates to a life-threatening condition that necessitates immediate intervention).

Figure 4:
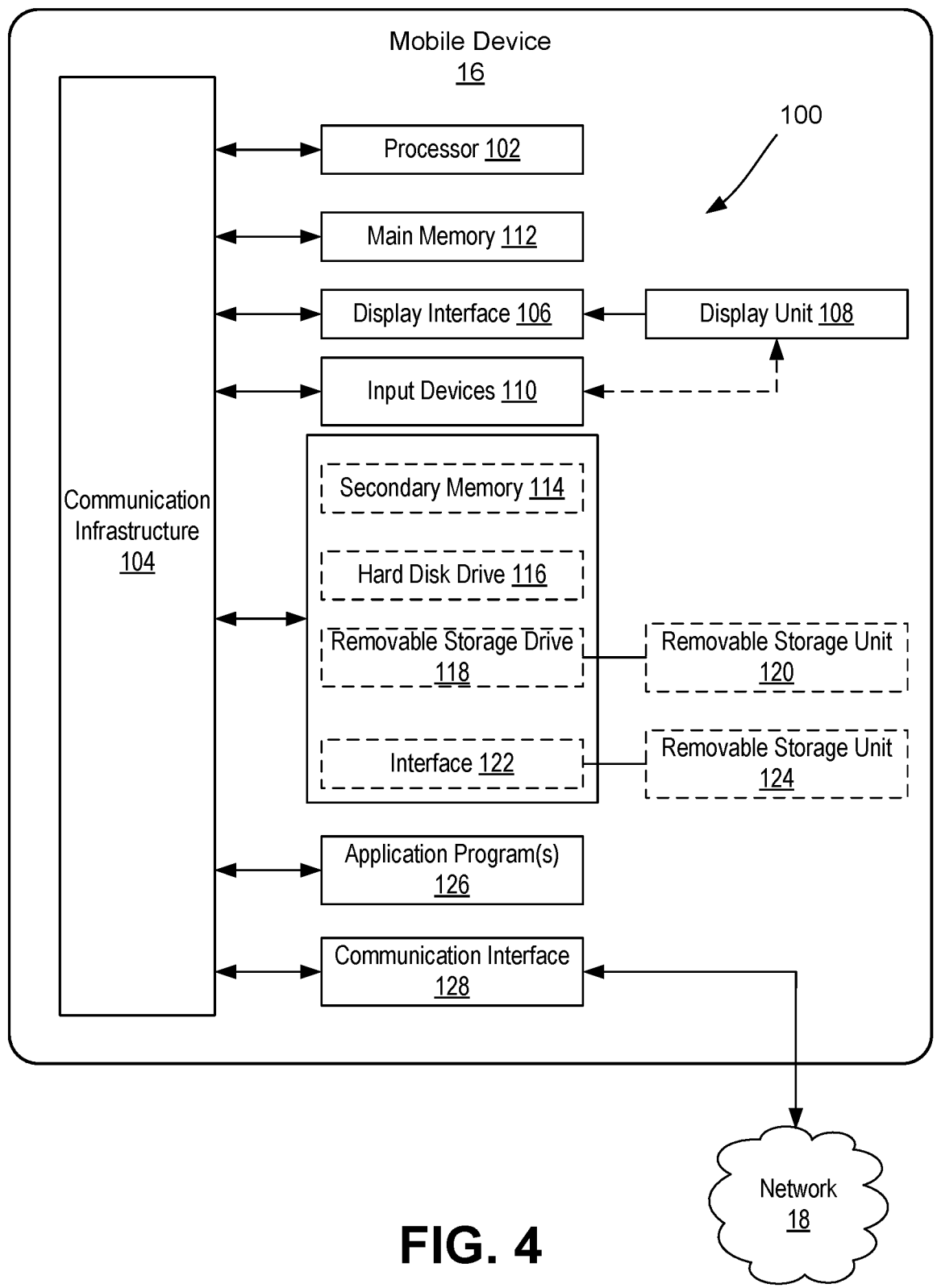
FIG. 4 is a block diagram illustrating at least one embodiment of a computing device (i.e., mobile device) for communicating with the health management platform and providing an interface upon which the user can interact so as to either participate with the injury recovery and/or injury prevention plan (i.e., an employee) and/or monitor health management information associated with such participation (i.e., an employer and/or care provider) and further communicate with others.

FIG. 4 is a block diagram illustrating at least one embodiment of a mobile device 16 for communicating with the health management platform 12 and providing an interface upon which the employee, employer, or care provider can interact so as to either participate with the injury recovery and/or injury prevention plan (i.e., an employee) and/or monitor health management information associated with such participation (i.e., an employer and/or care provider) and further communicate with others.

The mobile device 16 generally includes a computing system 100. As shown, the computing system 100 includes one or more processors, such as processor 102. Processor 102 is operably connected to communication infrastructure 304 (e.g., a communications bus, cross-over bar, or network). The processor 102 may be embodied as any type of processor capable of performing the functions described herein. For example, the processor may be embodied as a single or multi-core processor(s), digital signal processor, microcontroller, or other processor or processing/controlling circuit.

The computing system 100 further includes a display interface 106 that forwards graphics, text, sounds, and other data from communication infrastructure 104 (or from a frame buffer not shown) for display on display unit 108. The computing system further includes input devices 110. The input devices 110 may include one or more devices for interacting with the mobile device 16, such as a keypad, microphone, camera, as well as other input components, including motion sensors, and the like. In one embodiment, the display unit 108 may include a touch-sensitive display (also known as "touch screens" or "touchscreens"), in addition to, or as an alternative to, physical push-button keyboard or the like. The touch screen may generally display graphics and text, as well as provides a user interface (e.g., but not limited to graphical user interface (GUI)) through which a user may interact with the mobile device 16, such as accessing and interacting with applications executed on the device 16, including an app for providing direct user input with the health management service offered by the health management platform.

The computing system 100 further includes main memory 112, such as random access memory (RAM), and may also include secondary memory 114. The main memory 112 and secondary memory 114 may be embodied as any type of device or devices configured for short-term or long-term storage of data such as, for example, memory devices and circuits, memory cards, hard disk drives, solid-state drives, or other data storage devices. Similarly, the memory 112, 114 may be embodied as any type of volatile or non-volatile memory or data storage capable of performing the functions described herein.

In the illustrative embodiment, the mobile device 16 may maintain one or more application programs, databases, media and/or other information in the main and/or secondary memory 112, 114. The secondary memory 114 may include, for example, a hard disk drive 116 and/or removable storage drive 118, representing a floppy disk drive, a magnetic tape drive, an optical disk drive, etc. Removable storage drive 318 reads from and/or writes to removable storage unit 120 in any known manner. The removable storage unit 120 may represents a floppy disk, magnetic tape, optical disk, etc. which is read by and written to by removable storage drive 118. As will be appreciated, removable storage unit 120 includes a computer usable storage medium having stored therein computer software and/or data.

In alternative embodiments, the secondary memory 114 may include other similar devices for allowing computer programs or other instructions to be loaded into the computing system 100. Such devices may include, for example, a removable storage unit 124 and interface 122. Examples of such may include a program cartridge and cartridge interface (such as that found in video game devices), a removable memory chip (such as an erasable programmable read only memory (EPROM), or programmable read only memory (PROM)) and associated socket, and other removable storage units 124 and interfaces 122, which allow software and data to be transferred from removable storage unit 124 to the computing system 100.

The computing system 100 further includes one or more application programs 126 directly stored thereon. The application program(s) 126 may include any number of different software application programs, each configured to execute a specific task.

The computing system 300 further includes a communications interface 128. The communications interface 128 may be embodied as any communication circuit, device, or collection thereof, capable of enabling communications between the mobile device 16 external devices (other mobile devices 16, the cloud-based service 14, including the health management platform). The communications interface 128 may be configured to use any one or more communication technology and associated protocols, as described above, to effect such communication. For example, the communications interface 128 may be configured to communicate and exchange data with the health management platform 12, and/or one other mobile device 16, via a wireless transmission protocol including, but not limited to, Bluetooth communication, infrared communication, near field communication (NFC), radio-frequency identification (RFID) communication, cellular network communication, the most recently published versions of IEEE 802.11 transmission protocol standards as of October 2018, and a combination thereof. Examples of communications interface 128 may include a modem, a network interface (such as an Ethernet card), a communications port, a Personal Computer Memory Card International Association (PCMCIA) slot and card, wireless communication circuitry, etc.

Computer programs (also referred to as computer control logic) may be stored in main memory 112 and/or secondary memory 114 or a local database on the mobile device 16. Computer programs may also be received via communications interface 128. Such computer programs, when executed, enable the computing system 100 to perform the features of the present invention, as discussed herein. In particular, the computer programs, including application programs 126, when executed, enable processor 102 to perform the features of the present invention. Accordingly, such computer programs represent controllers of computer system 100.

In one embodiment where the invention is implemented using software, the software may be stored in a computer program product and loaded into the computing system 100 using removable storage drive 118, hard drive 116 or communications interface 128. The control logic (software), when executed by processor 102, causes processor 102 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

Figure 5:
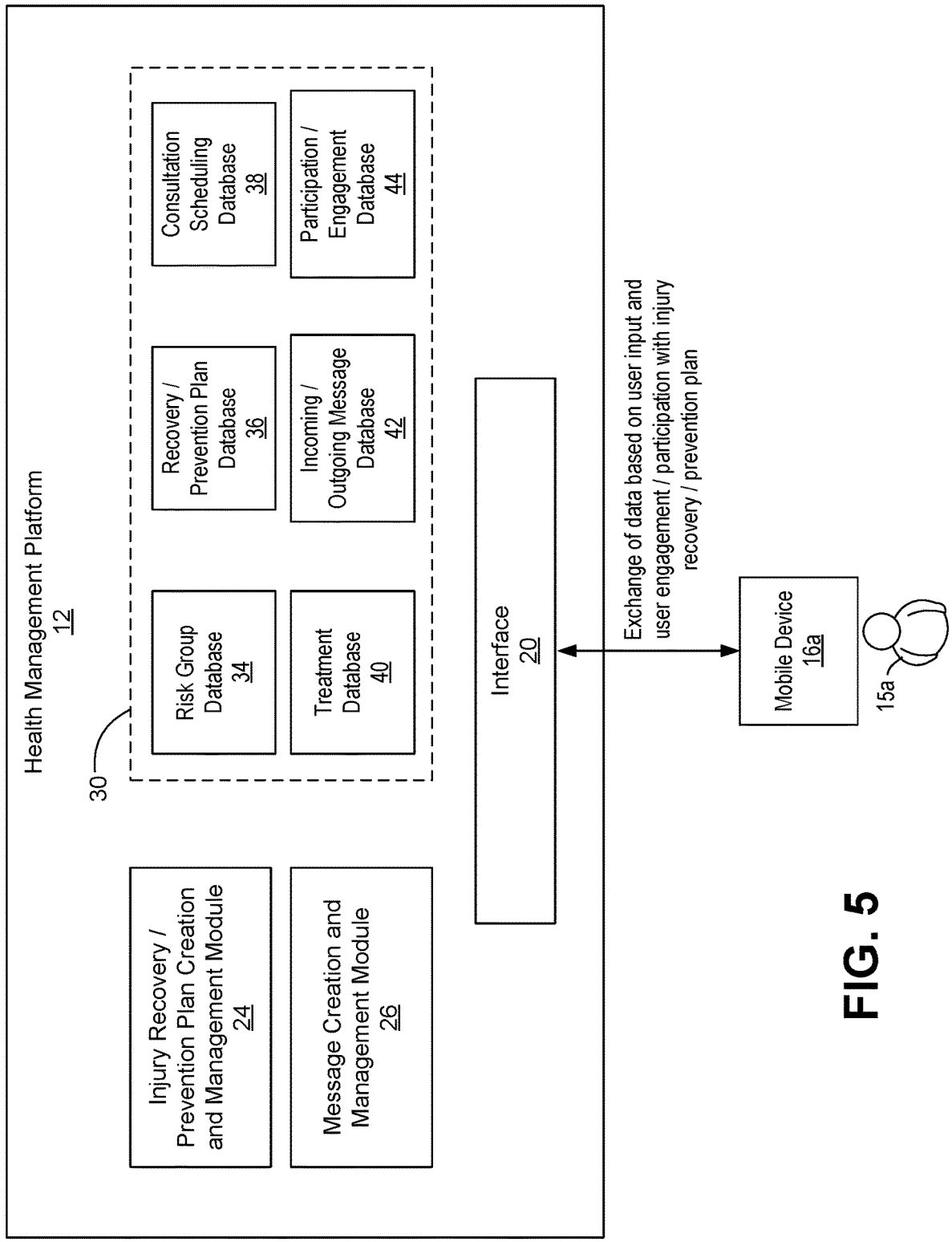
FIG. 5 is a block diagram illustrating communication and exchange of data between a mobile device of an employee and the health management platform consistent with the present disclosure.

FIG. 5 is a block diagram illustrating communication and exchange of data between a mobile device 16*a* of an employee and the health management platform 12 consistent with the present disclosure. As previously described, the health management platform 12 is configured to generate injury recovery and/or injury prevention plans tailored to the employee based on specific data provided. The platform is further configured to monitor the employee's participation and engagement with the injury recovery and/or injury prevention plan based, at least in part, on the employee's interaction with at least one of the physical recovery and psychosocial health components, which may include attending the suggested consultations or appointments (which may include in-person visits, telephone calls, text messaging, or video conferencing), attempting/completing the treatments/exercises, and participating in the message exchanges (i.e., responding to received communications).

As such, the platform 12 is configured to receive feedback indicating whether the employee has attended the one or more suggested consultations with the care provider, whether the employee has started and/or completed the one or more suggested injury recovery and/or injury prevention treatments, and further receive one or more responses from the employee to one or more communication messages transmitted to the employee. The feedback data may be stored in the respective databases, including the participation/engagement database 44. In particular, the platform 12 may be configured to further track participation and engagement data, including aggregating and storing the participation and engagement data in database 44.

In some embodiments, the platform 12 may be configured to modify (i.e., adjust) the injury recovery and/or injury prevention plan based on real-time analysis of the employee's feedback and/or the one or more responses from the employee. The adjustments to the injury recovery and/or injury prevention plan may include one or more adjustments to the physical recovery component and/or psychosocial component including, but not limited to, adjusting frequency of the one or more initially suggested consultations with a care provider, updating the plan to include one or more additional suggested consultations with one or more additional care providers, updating the plan to include one or more additional suggested injury recovery and/or injury prevention treatments, updating the plan to remove the one or more initially suggested injury recovery and/or injury prevention treatments, adjusting frequency of the one or more communication messages to be transmitted to the employee, and adjusting the content of the one or more communication messages to be transmitted to the employee. In some embodiments, the platform 12 may be configured to re-stratify the employee into one of the plurality of risk groups based on real-time analysis of the employee's feedback and/or the one or more responses from the employee.

Figure 6:
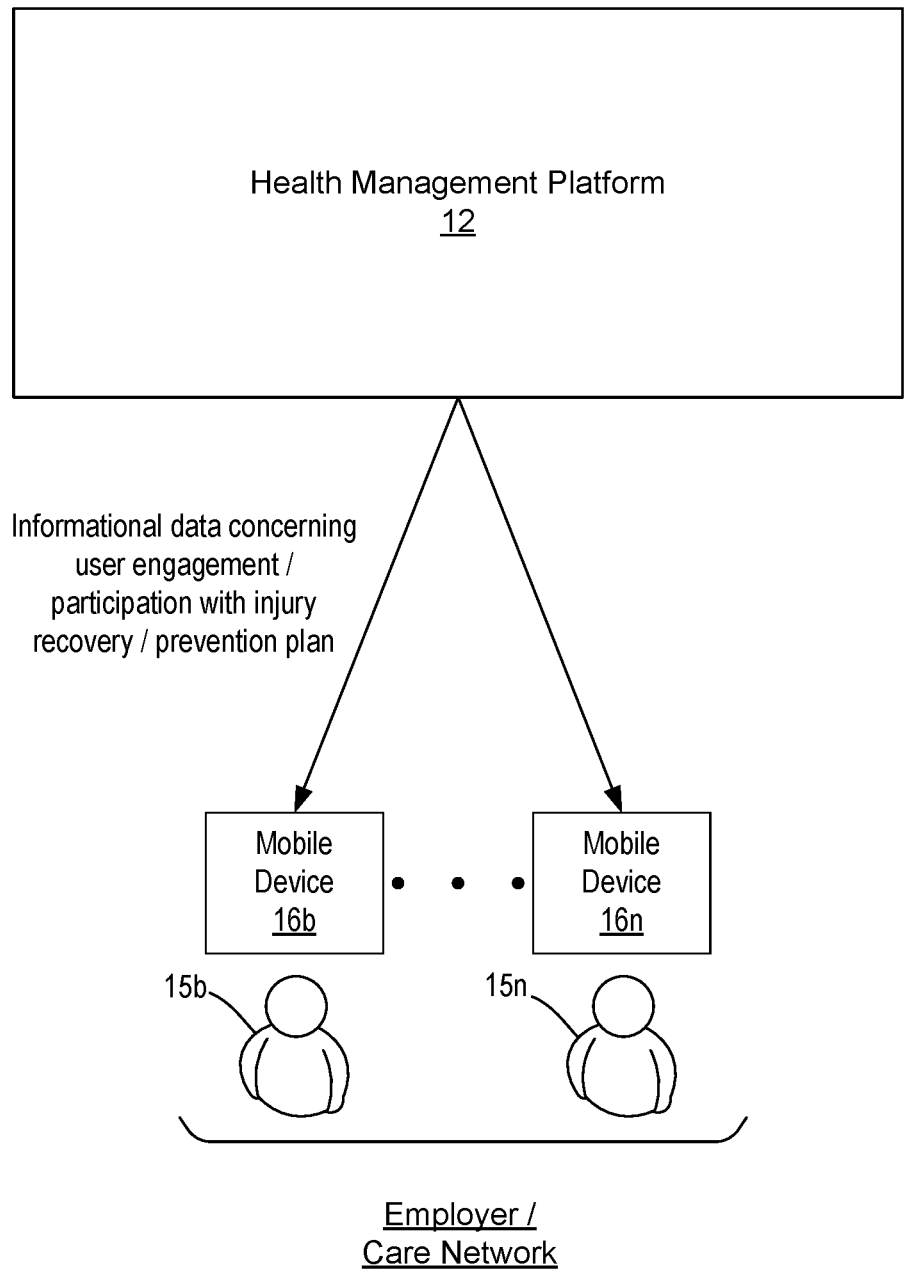
FIG. 6 is a block diagram illustrating communication and exchange of data between a mobile device of an employer and/or care provided and the health management platform.

FIG. 6 is a block diagram illustrating communication and exchange of data between a mobile device of an employer and/or care provided and the health management platform 12. As previously described, the platform 12 further includes at least a second web portal or UI with which an employer or care provider associated with the employee may interact, via an associated computing device (illustrated as a mobile device), so as to monitor the employee's progress and participation with the plan. It should be noted that the platform 12 is configured to restrict access to data associated with the employee, including employee participation for any given injury recovery and/or injury prevention plan, based, at least in part, on a level of authority associated with the employer or care provider requesting access to the data. For example, upon receiving a request from the employer or care provider for access to any data associated with the employee, the security management module 28 is configured to compare request data with one or more authorized user profiles (stored in the user database 32) and, in some instances, compared with one or more profiles in the role database 46, to determine a level of access to data associated with the employee for the employer or care provider. Upon a positive correlation of the request data with an authorized profile, the security management module 28 is configured to grant the employer or care provider access to the data associated with the employee.

In particular, the platform 12 provides a suite of features to keep both the employee and the employer and/or care providers in continuous contact and engaged with one another, thereby providing the employee with the feeling of support in their recovery process, as opposed to simply providing recovery exercises and treatments and expecting the employee to complete the plans. For example, the platform 12 further allows allow employers and/or care providers to maintain continuous engagement with the employee, either by way of fully-automated, or semi-automated, or fully personalized communications to ensure that personal attention is provided to the employee as needed, such as answering any questions the employee may have, as well as following up with the employee to see how they are feeling, physically and/or mentally. The platform also allows for the scheduling of events included in the injury recovery and/or injury prevention plan, such as appointments/consultations with care providers, specific physical treatments or exercises, and the like, and further provides reminders/alerts to the employee of such events so as to keep the employee on track. The platform 12 further allows for the employer and/or care provider to modify the plan as needed.

Figure 7:
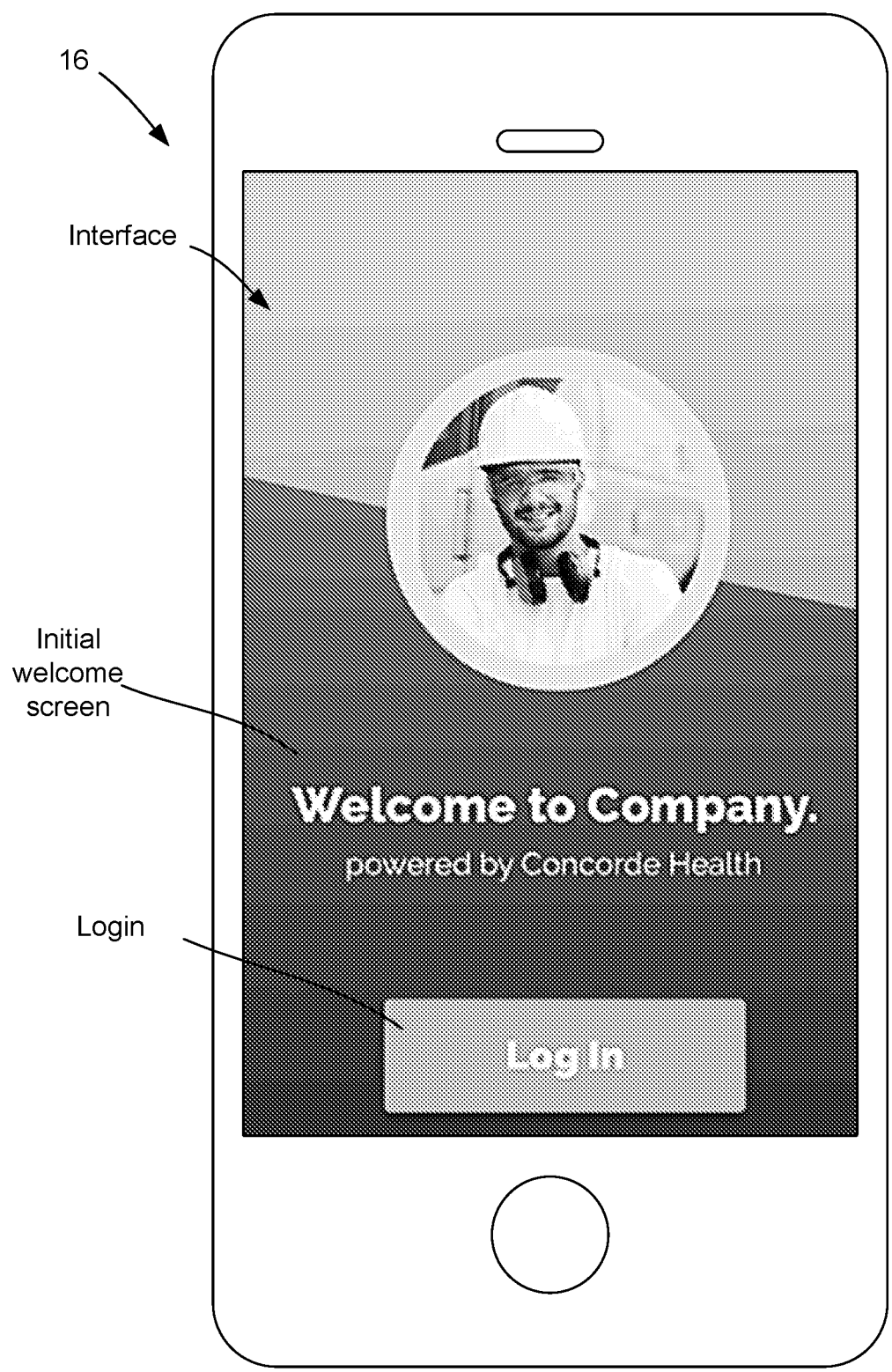
FIG. 7 is a screenshot of an interface on a mobile device associated with the health management services provided by the health management platform of the present disclosure, in which an initial login and/or registration screen is provided.

FIG. 7 is a screenshot of an interface on a mobile device associated with the health management services provided by the health management platform of the present disclosure, in which an initial login and/or registration screen is provided.

Figures 8A, 8B, 8C, 8D:
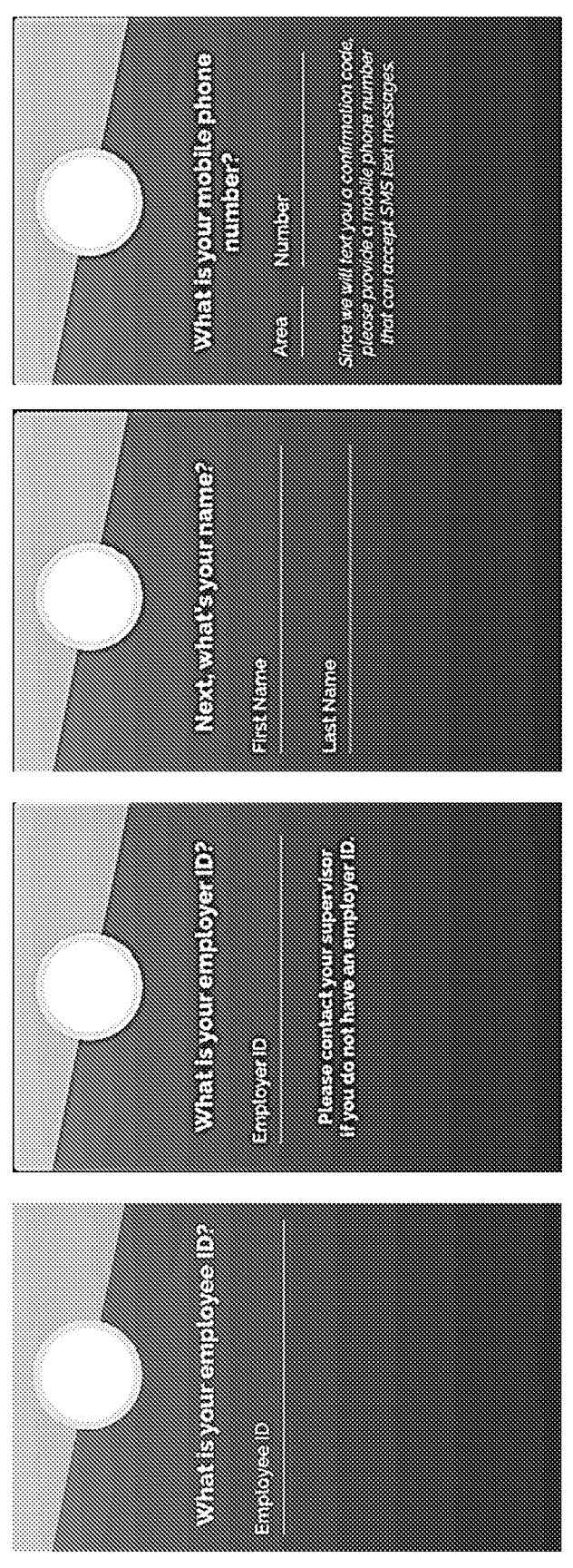
Figure 8H:
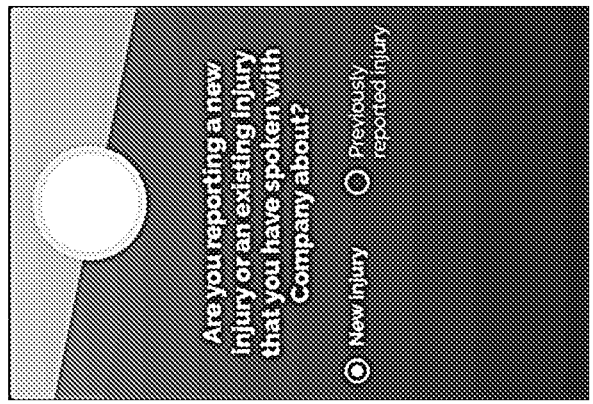
FIGS. 8A-8P are screenshots of an interface on a mobile device illustrating a registration/login sequence, reporting of an injury and details associated therewith, and a subsequent scheduling of an appointment.
Figure 8G:
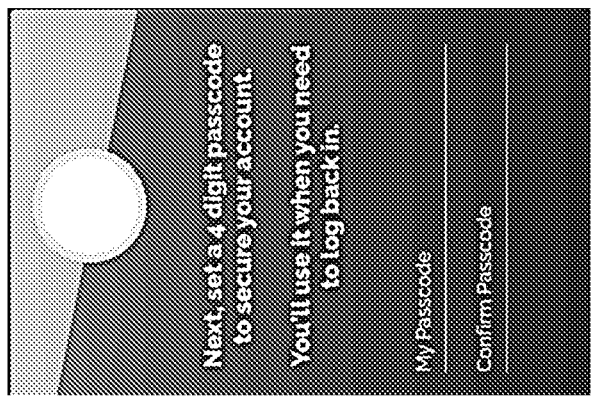
Figure 8F:
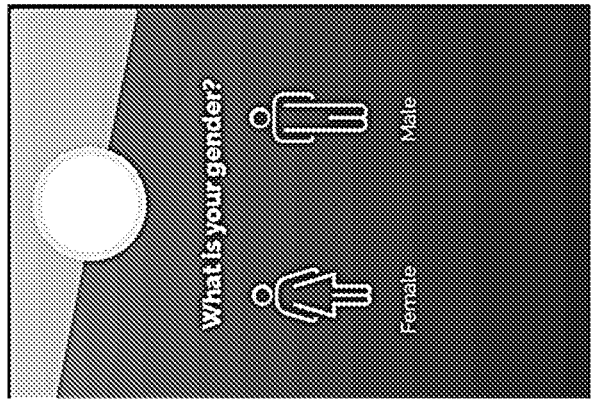
Figure 8E:
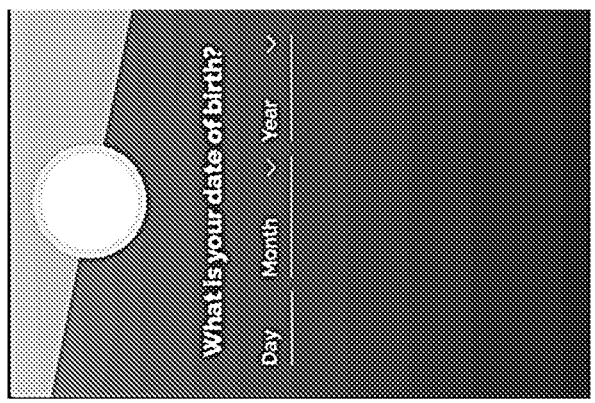
Figure 8L:
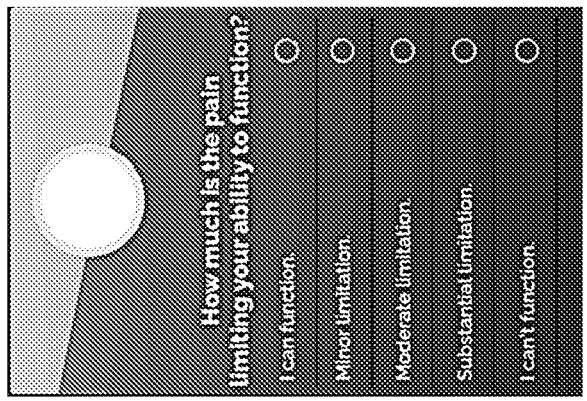
Figure 8K:
Figure 8J:
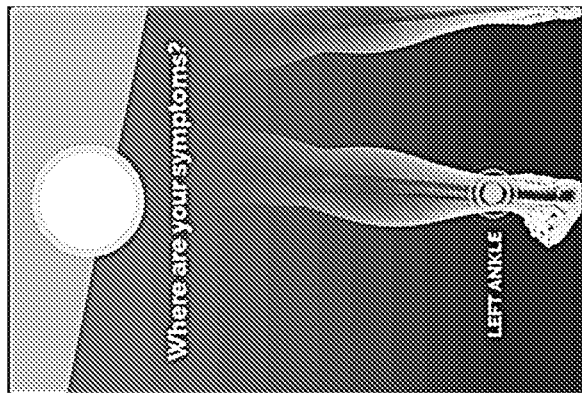
Figure 8I:
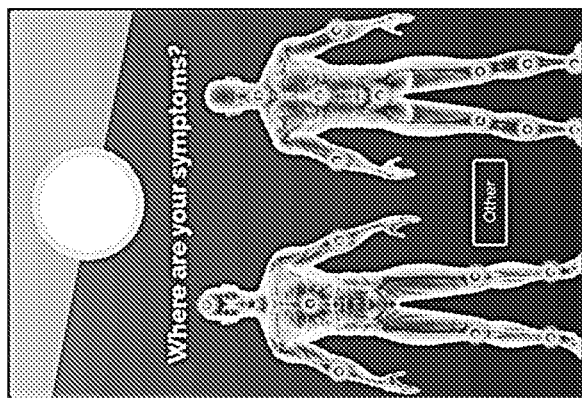
Figure 8M:
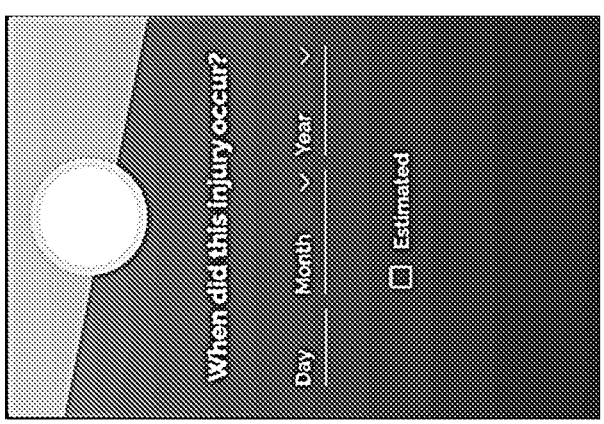
Figure 8N:
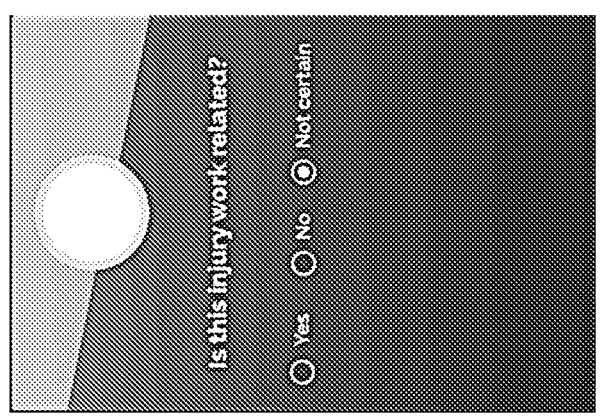
Figure 8O:
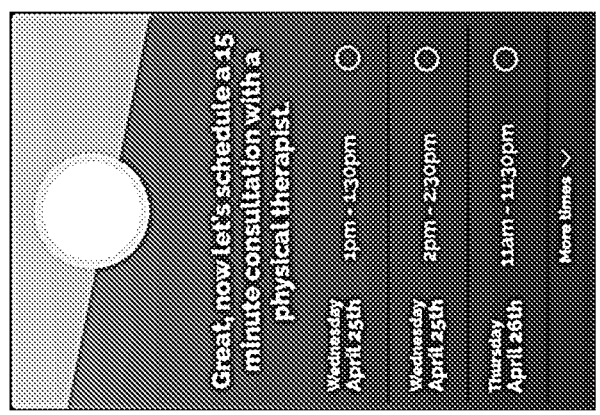
Figure 8P:
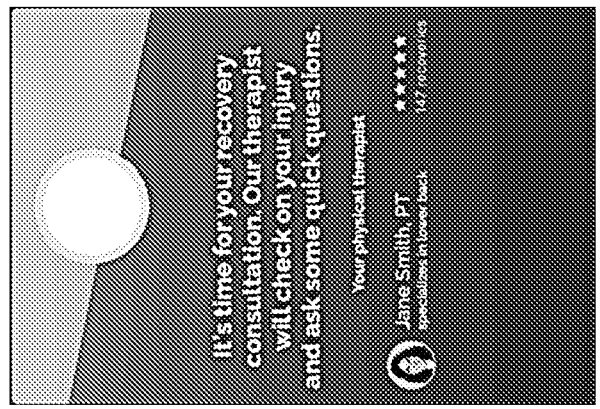

FIGS. 8A-8P are screenshots of an interface on a mobile device illustrating a registration/login sequence, reporting of an injury and details associated therewith, and a subsequent scheduling of an appointment.

Figure 9:
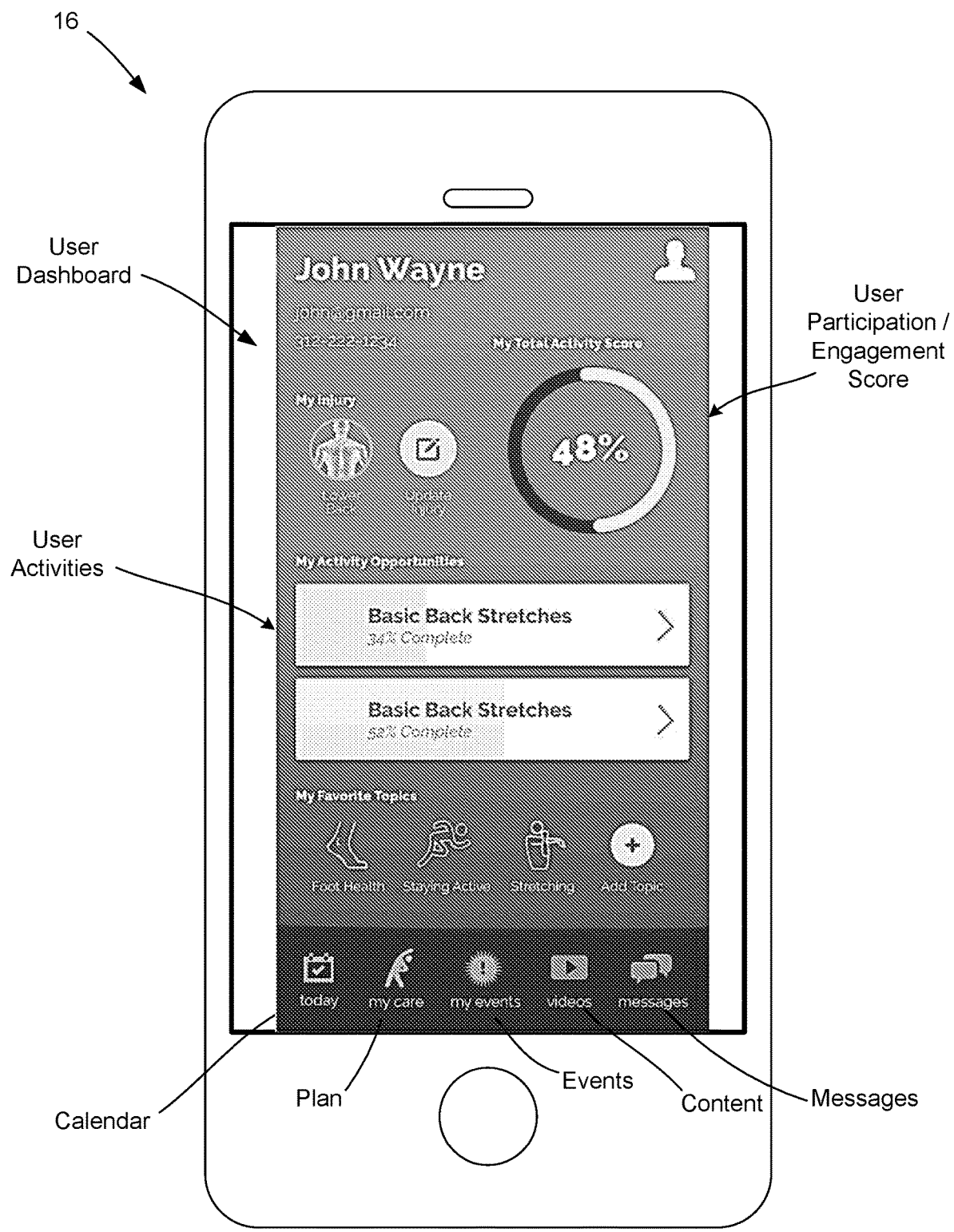
FIG. 9 is a screenshot of an exemplary user dashboard/hub associated with the health management services provided by the health management platform of the present disclosure, in which a user is able to view information related to their specific plan, including progress/participation, as well as select from and interact with a variety of content, including a calendar of scheduled events, specific treatments and/or exercises associated with the injury recovery and/or injury prevention plan, including any form of media (i.e., image file, video file, audio file, document file, etc.), and messages (incoming and outgoing messages received from or delivered to the user).

FIG. 9 is a screenshot of an exemplary user dashboard/hub associated with the health management services provided by the health management platform of the present disclosure, in which a user is able to view information related to their specific plan, including progress/participation, as well as select from and interact with a variety of content, including a calendar of scheduled events, specific treatments and/or exercises associated with the injury recovery and/or injury prevention plan, including any form of media (i.e., image file, video file, audio file, document file, etc.), and messages (incoming and outgoing messages received from or delivered to the user).

Figure 10C:
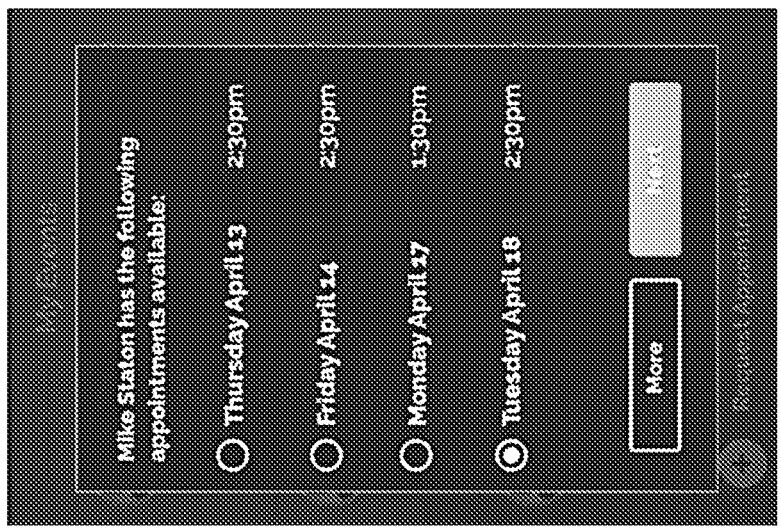
FIGS. 10A-10C are screenshots of an interface on a mobile device illustrating a sequence of scheduling an appointment with a care provider.
Figure 10B:
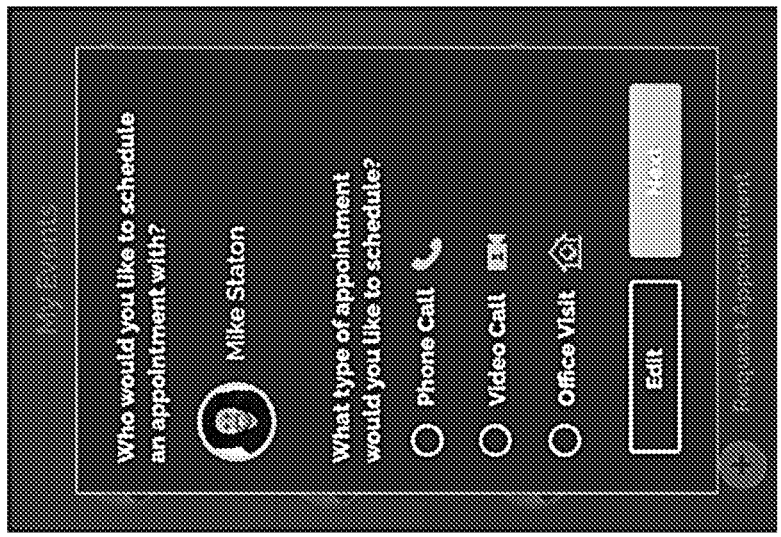
Figure 10A:
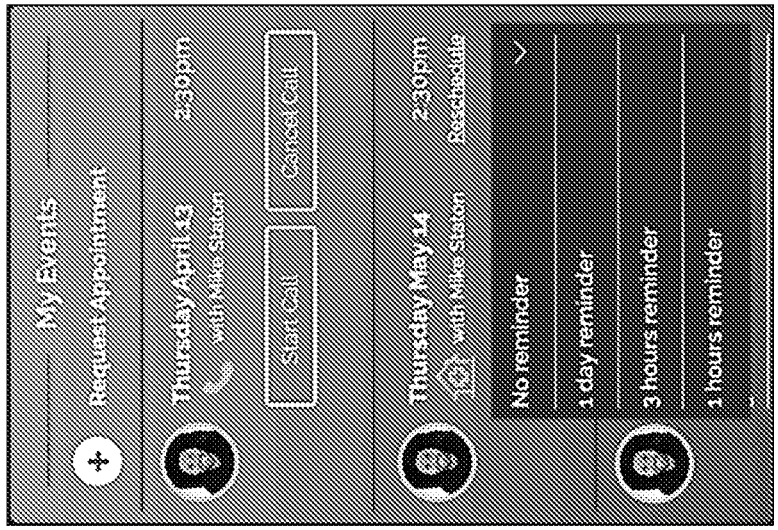

FIGS. 10A-10C are screenshots of an interface on a mobile device illustrating a sequence of scheduling an appointment with a care provider.

Figure 11:
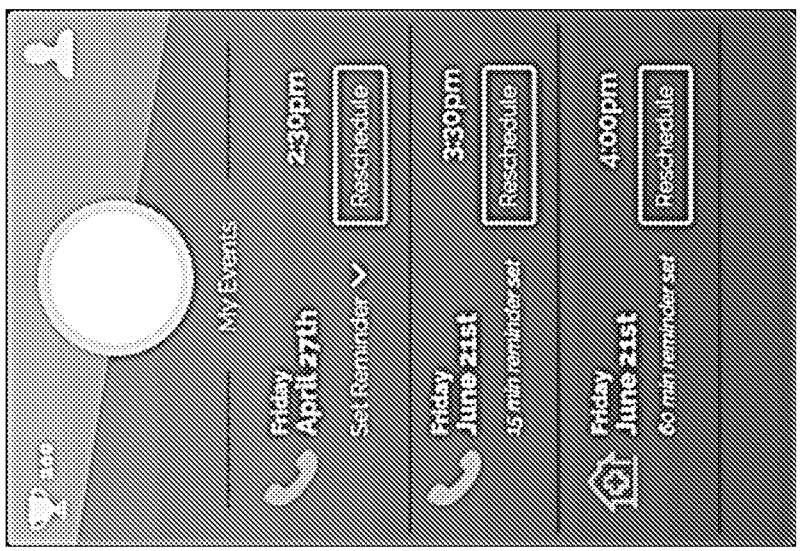
FIG. 11 is a screenshot of an interface on a mobile device illustrating a listing of events for a user associated with their injury recovery and/or injury prevention plan.

FIG. 11 is a screenshot of an interface on a mobile device illustrating a listing of events for a user associated with their injury recovery and/or injury prevention plan.

Figure 12:
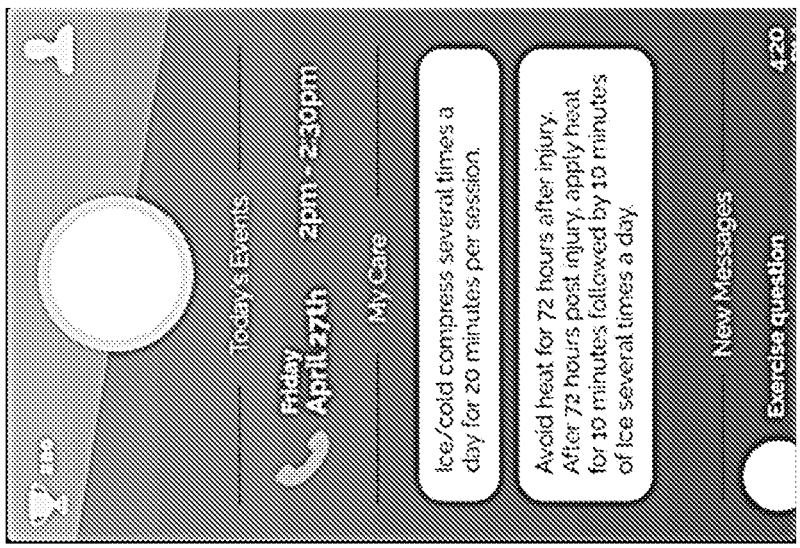
FIG. 12 is a screenshot of an interface on a mobile device illustrating a specific care plan event detailing a treatment (provided in a message form) for the user to perform.

FIG. 12 is a screenshot of an interface on a mobile device illustrating a specific care plan event detailing a treatment (provided in a message form) for the user to perform.

Figure 13:
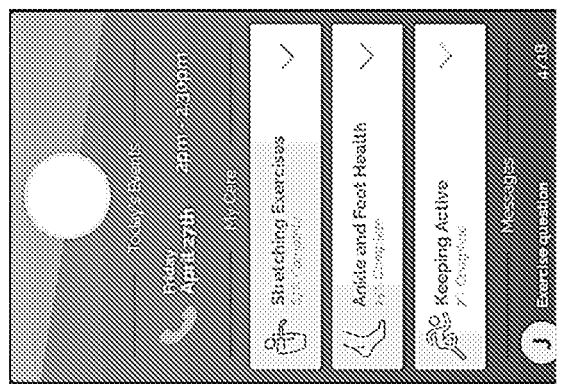
FIG. 13 is a screenshot of an interface on a mobile device illustrating exemplary care plan events, including a physical exercise component in the form of videos and illustrations and literature providing information regarding the injury.

FIG. 13 is a screenshot of an interface on a mobile device illustrating exemplary care plan events, including a physical exercise component in the form of videos and illustrations and literature providing information regarding the injury.

Figure 14C:
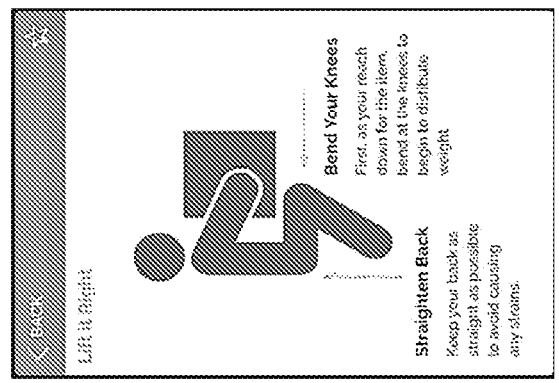
FIGS. 14A-14C are screenshots of an interface on a mobile device illustrating various videos providing physical exercises for the user to complete and an illustration of proper form when performing certain movements (lifting objects).
Figure 14B:
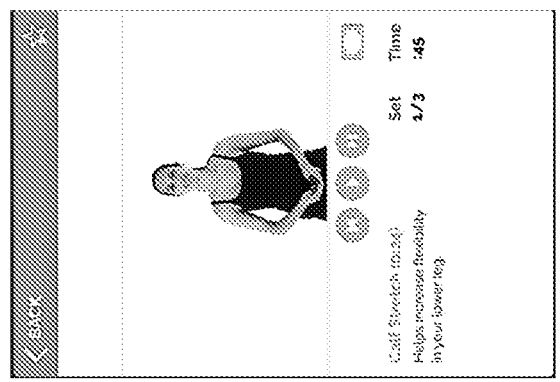
Figure 14A:
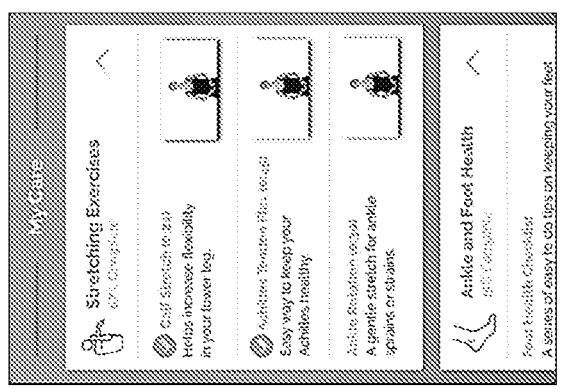

FIGS. 14A-14C are screenshots of an interface on a mobile device illustrating various videos providing physical exercises for the user to complete and an illustration of proper form when performing certain movements (lifting objects).

Figures 15A, 15B, 15C:
FIGS. 15A-15C are screenshots of an interface on a mobile device illustrating an interactive checklist and quiz providing health-related information to the user regarding the injury.

FIGS. 15A-15C are screenshots of an interface on a mobile device illustrating an interactive checklist and quiz providing health-related information to the user regarding the injury.

Figure 16:
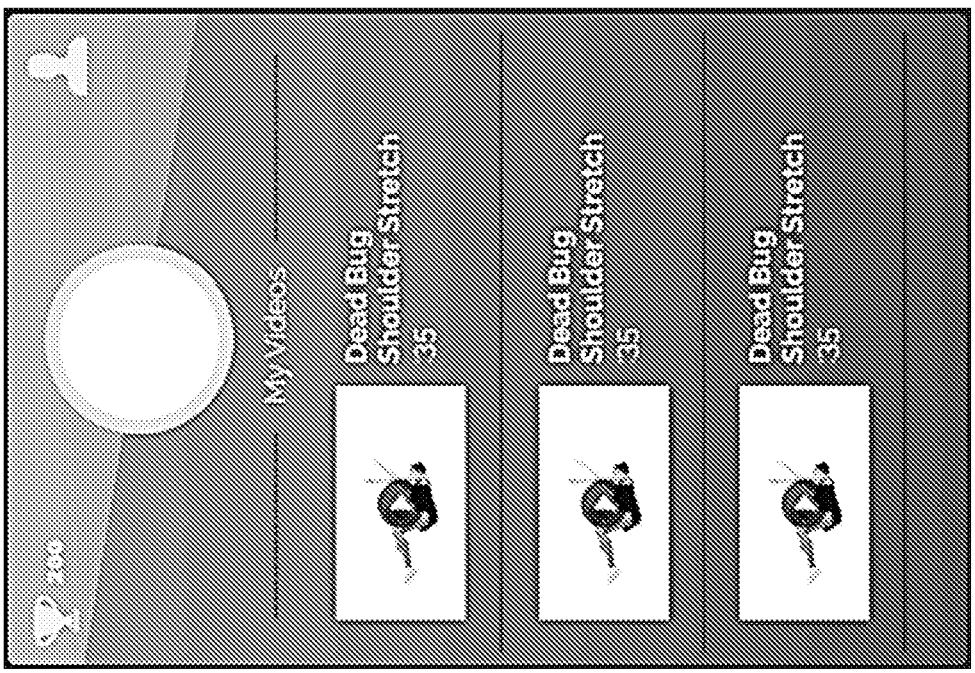
FIG. 16 is a screenshot of an interface on a mobile device illustrating video content providing physical exercises to be performed by the user.

FIG. 16 is a screenshot of an interface on a mobile device illustrating video content providing physical exercises to be performed by the user.

Figure 17:
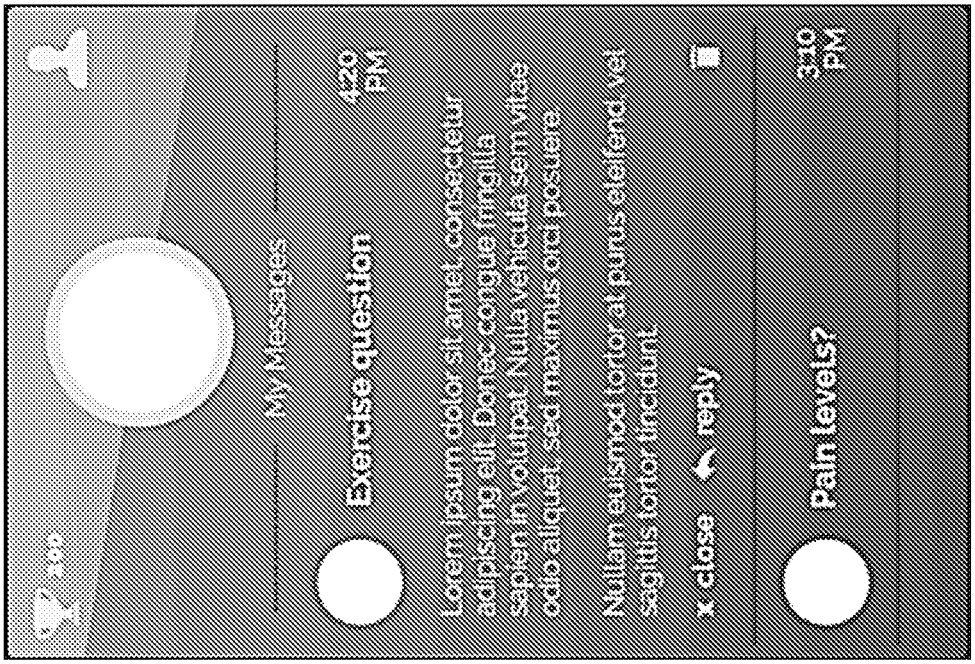
FIG. 17 is a screenshot of an interface on a mobile device illustrating a messages exchanged between the user (employee) and additional users associated therewith (i.e., employer or care providers).

FIG. 17 is a screenshot of an interface on a mobile device illustrating a messages exchanged between the user (employee) and additional users associated therewith (i.e., employer or care providers).

Figure 18:
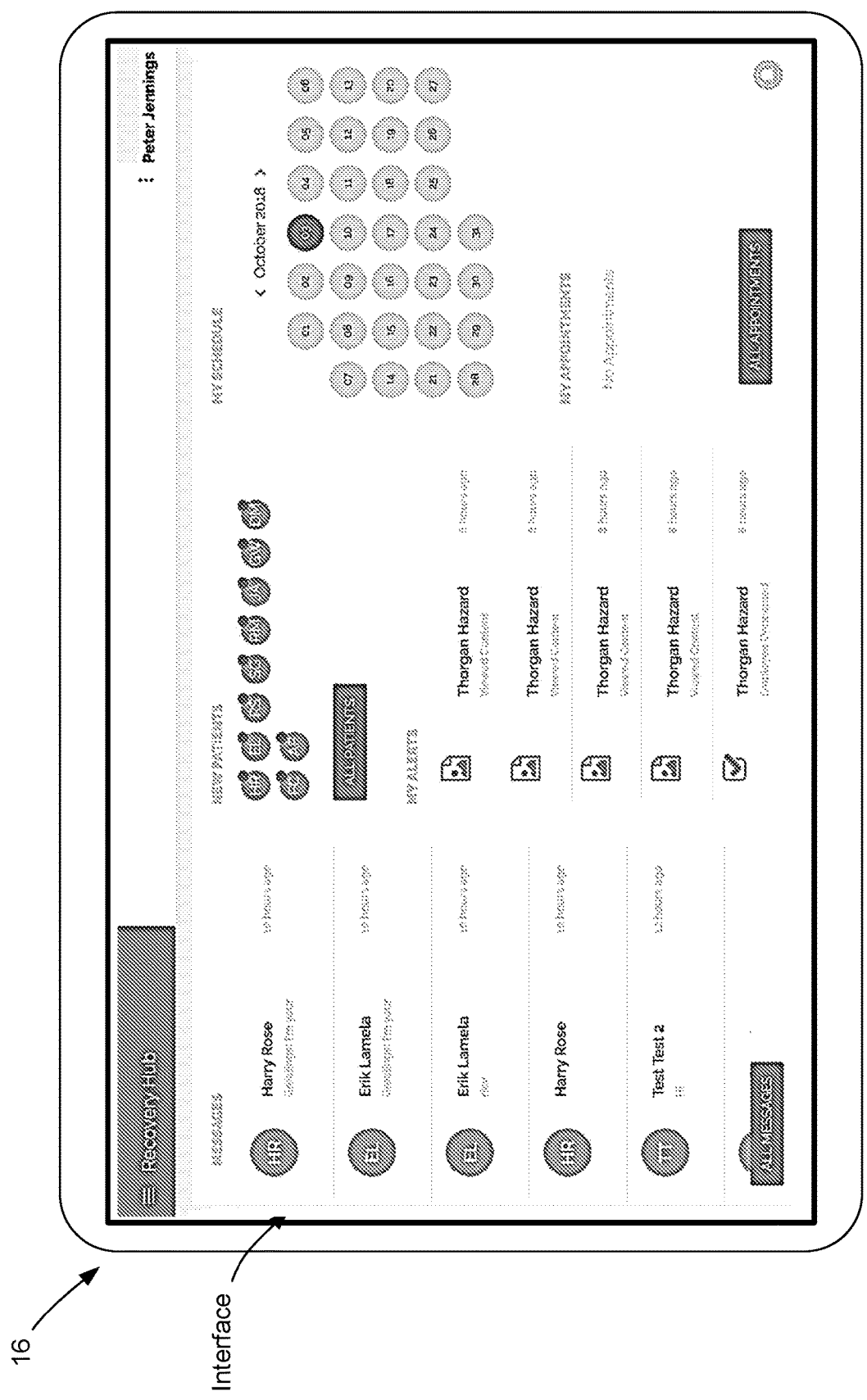
FIG. 18 is a screenshot of an exemplary user dashboard/hub associated with the health management services provided by the health management platform of the present disclosure, in which a user (i.e., employer or care provider) is able to view health information of individuals to which they have authority to monitor and/or interact with. The exemplary user dashboard is customized to a care provider and illustrates all patients under their care or to whom have been referred and are currently treating.

FIG. 18 is a screenshot of an exemplary user dashboard/hub associated with the health management services provided by the health management platform of the present disclosure, in which a user (i.e., employer or care provider) is able to view health information of individuals to which they have authority to monitor and/or interact with. The exemplary user dashboard is customized to a care provider and illustrates all patients under their care or to whom have been referred and are currently treating.

Figure 19:
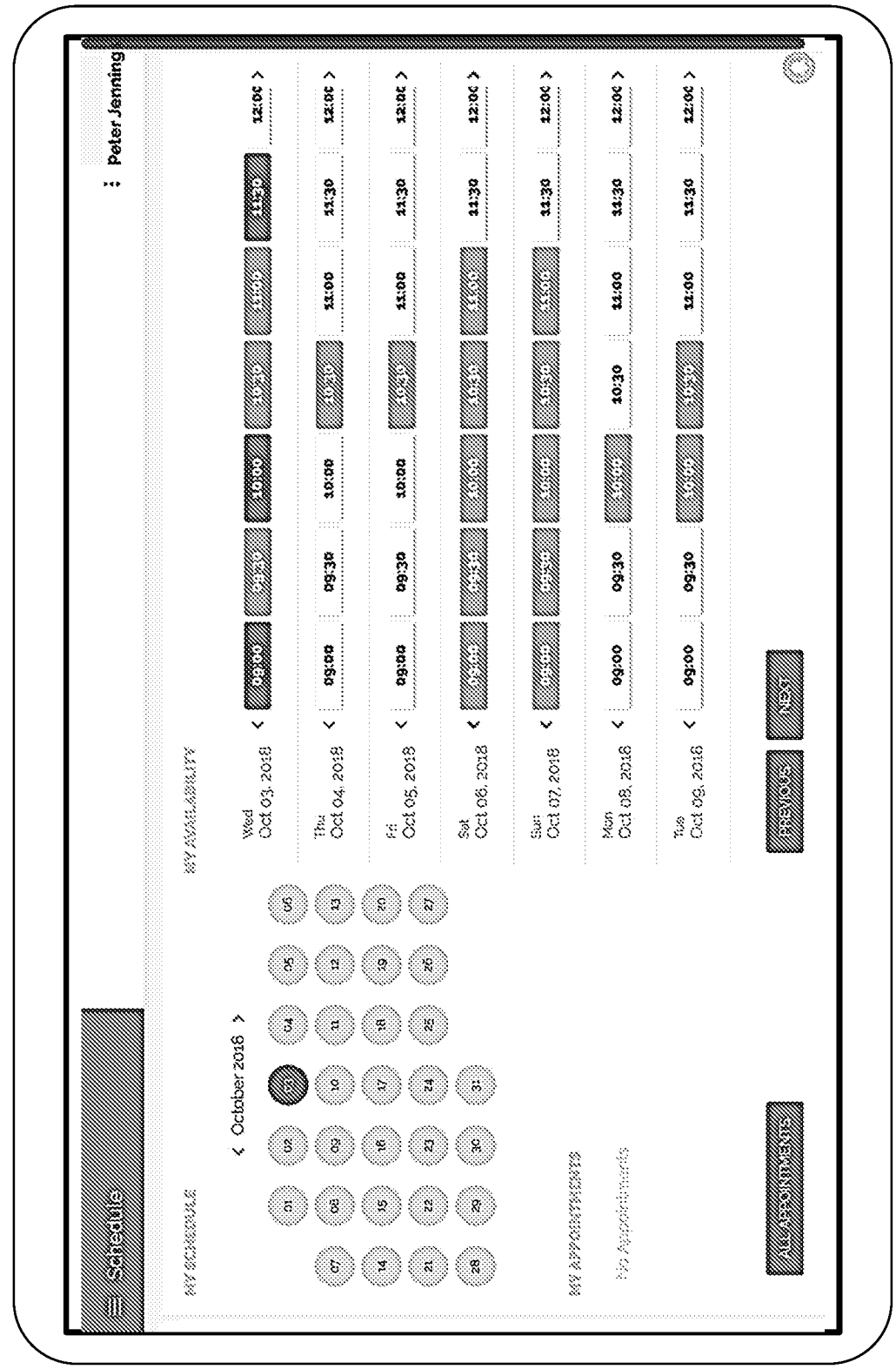
FIG. 19 is a screenshot of an interface in which the care provider can view their calendar/schedule and view specific appointments with any given patient.

FIG. 19 is a screenshot of an interface in which the care provider can view their calendar/schedule and view specific appointments with any given patient.

Figure 20:
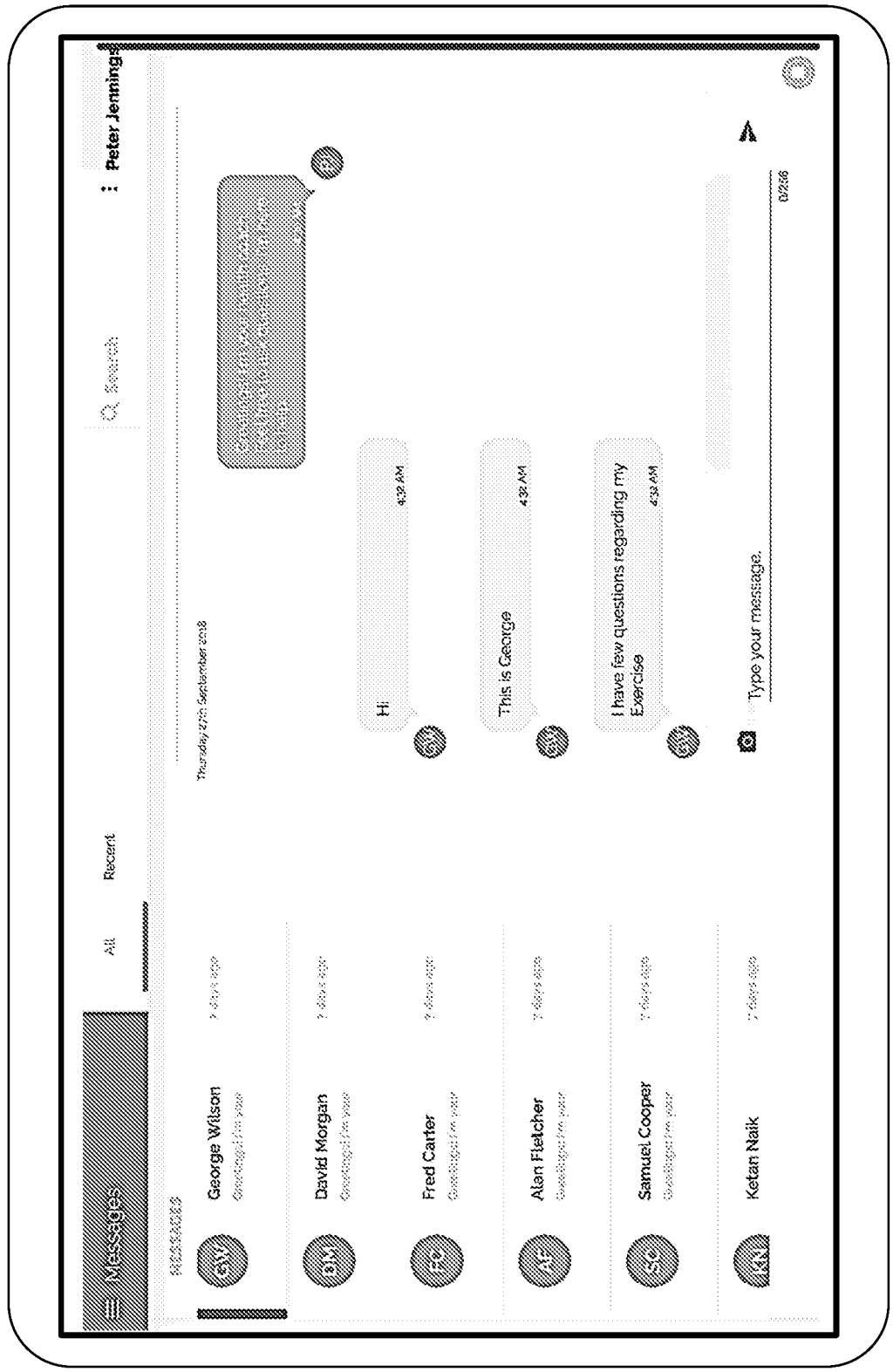
FIG. 20 is a screenshot of an interface in which the care provider can view messages from any patient and further communicate (i.e., send and receive messages) with patients.

FIG. 20 is a screenshot of an interface in which the care provider can view messages from any patient and further communicate (i.e., send and receive messages) with patients.

Figure 21:
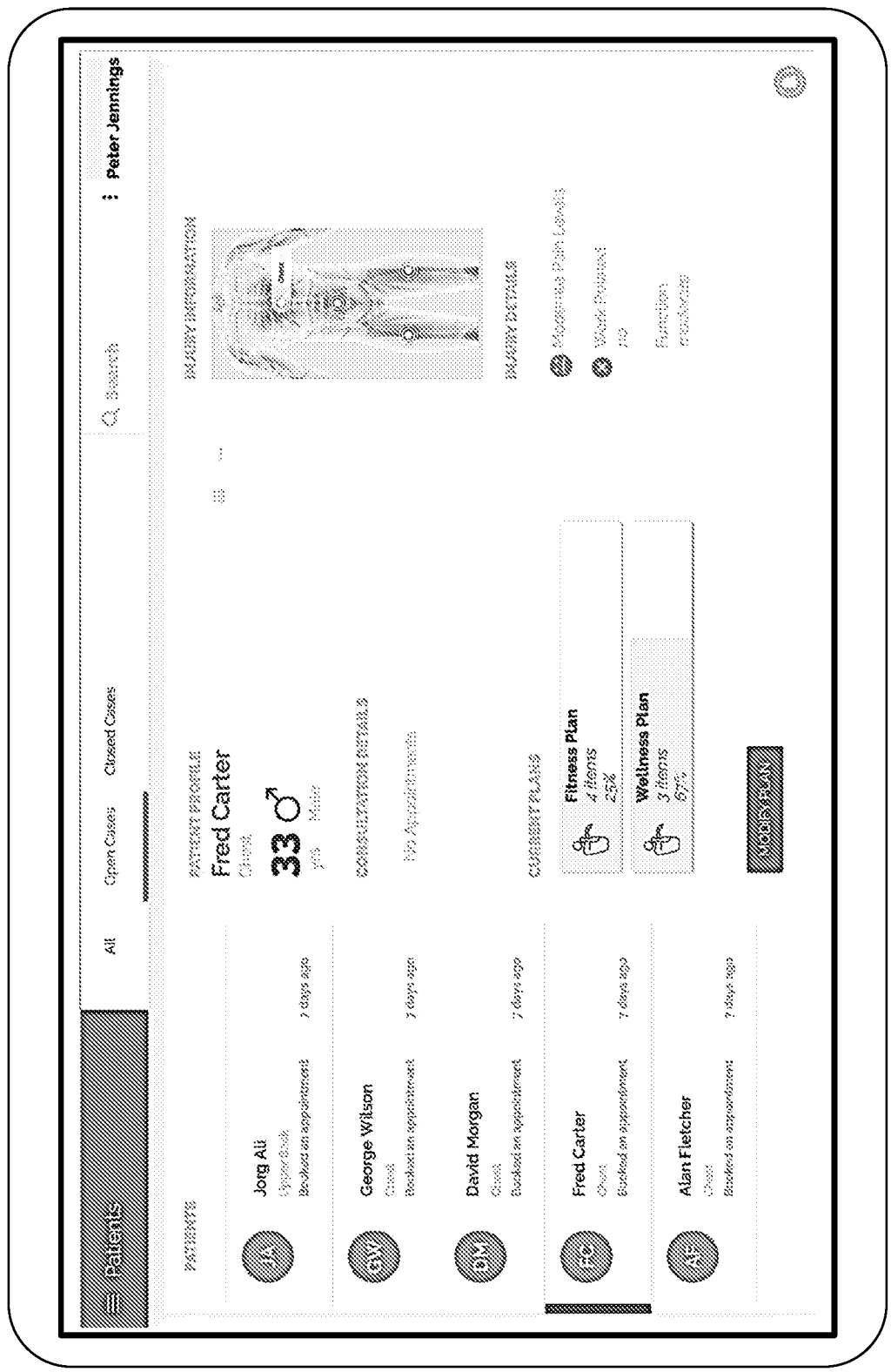
FIG. 21 is a screenshot of an interface in which the care provider can select any given patient and view information/details regarding that patient's injury recovery and/or injury prevention plan, including the patient's progress/participation with the plan.
Figure 22:
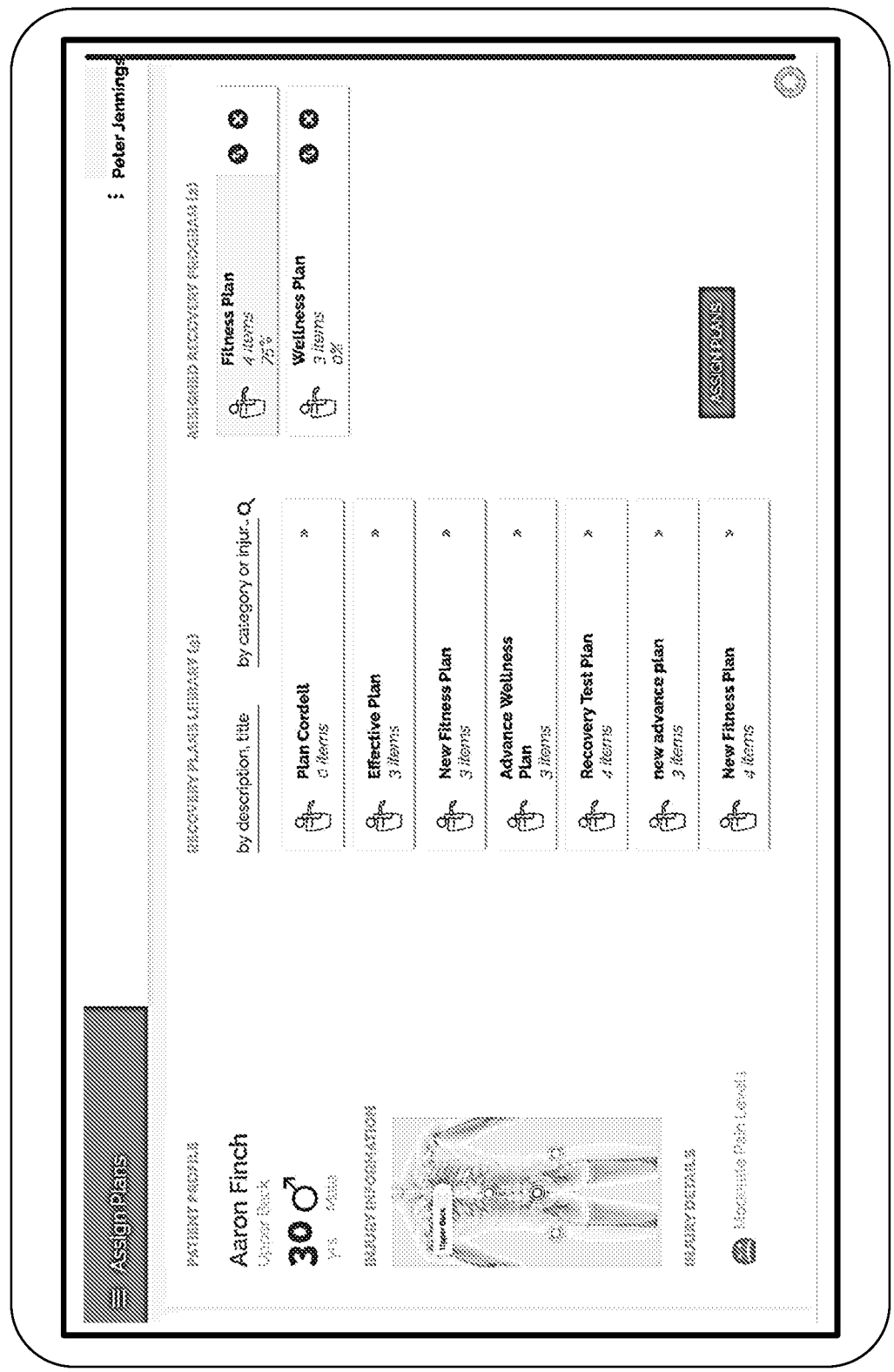
FIGS. 22-25 are screenshots of interfaces in which the care provider can assign specific plans to a given patient, each plan having at least one of a physical recovery component and a psychosocial health component, and further update/modify a plan (i.e., add or remove content to any given plan).
Figure 23:
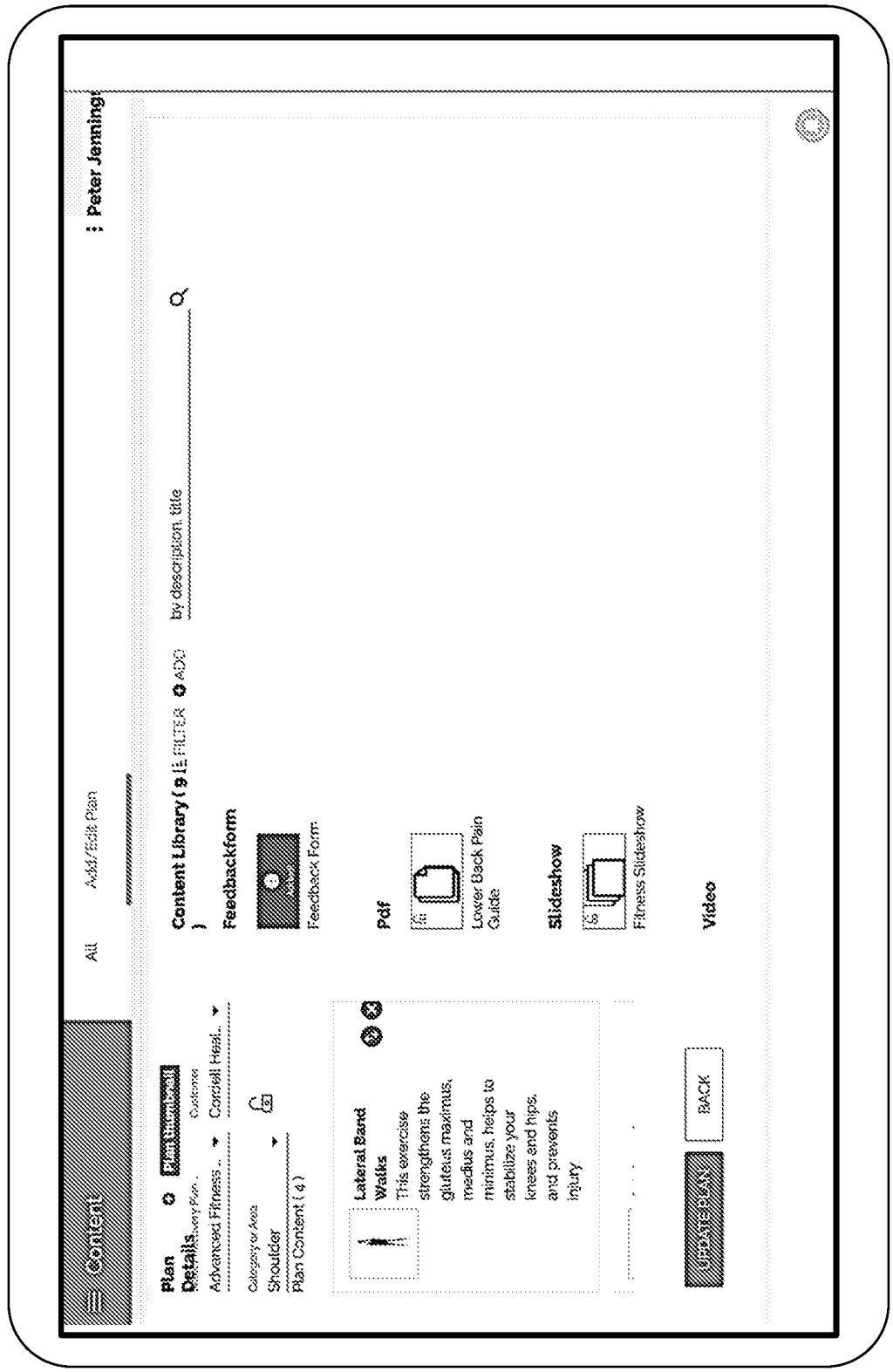
Figure 24:
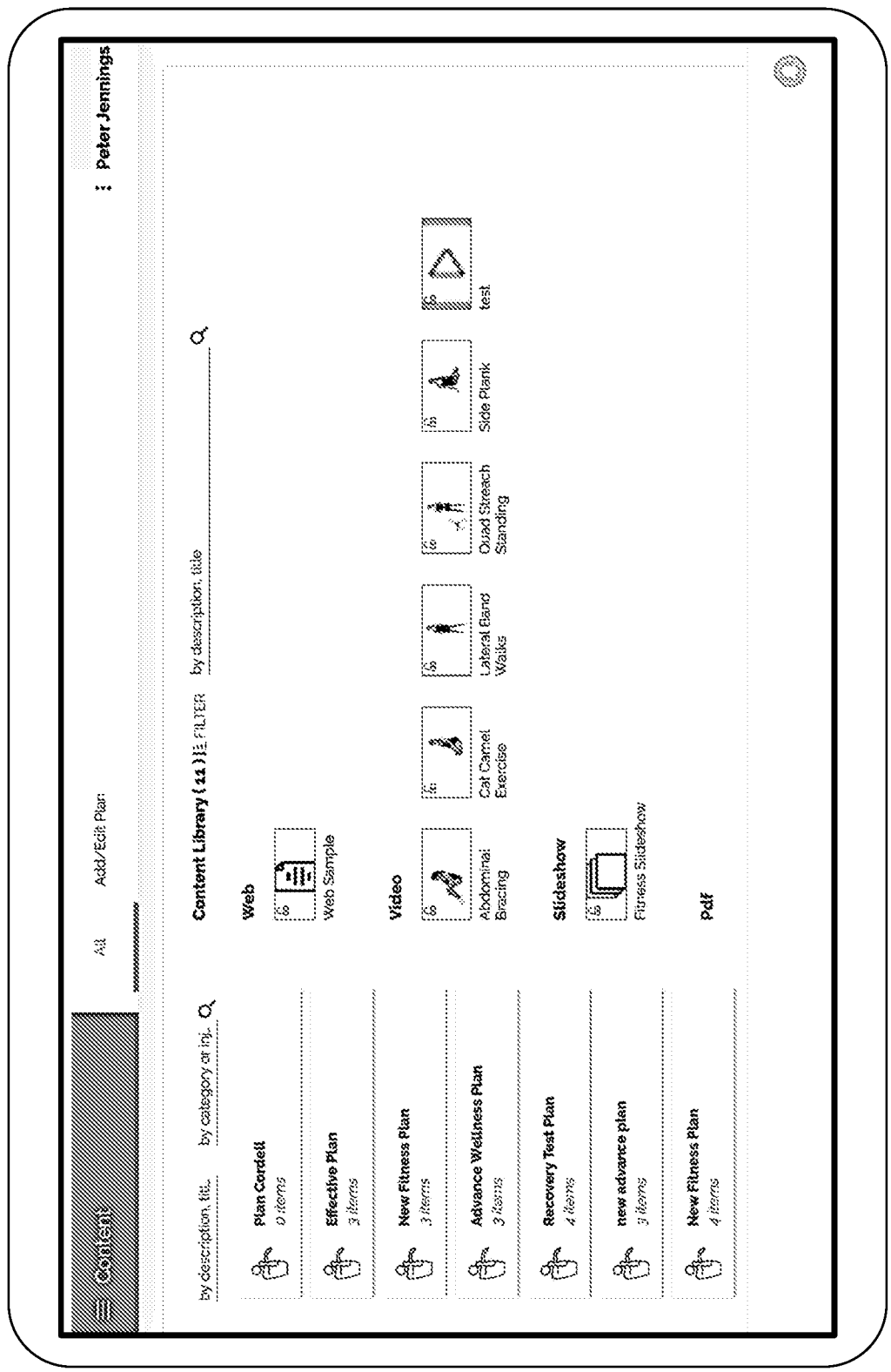
Figure 25:
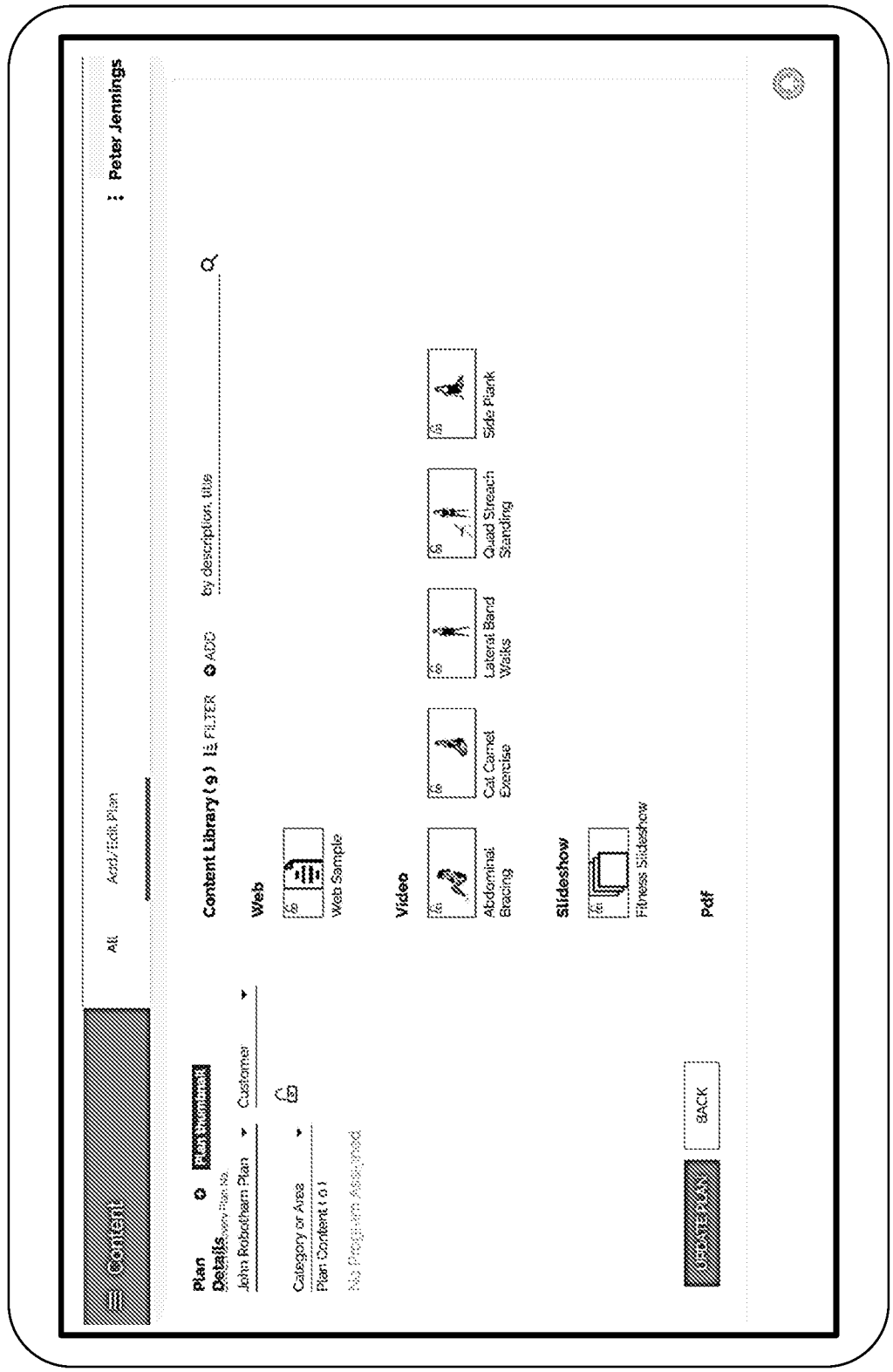

FIG. 21 is a screenshot of an interface in which the care provider can select any given patient and view information/details regarding that patient's injury recovery and/or injury prevention plan, including the patient's progress/participation with the plan.

FIGS. 22-25 are screenshots of interfaces in which the care provider can assign specific plans to a given patient, each plan having at least one of a physical recovery component and a psychosocial health component, and further update/modify a plan (i.e., add or remove content to any given plan).

As used in any embodiment herein, the term "module" may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The modules may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A system for providing health management services, the system comprising a computer server configured to:
receive, from a first user, first user data associated with an injury of the first user;
stratify, based on the first user data, the first user into one of a plurality of risk groups, each risk group associated with a respective level of guidance and care provider involvement in order to facilitate the first user's compliance with an injury recovery and/or injury prevention plan; and
generate the injury recovery and/or injury prevention plan tailored to the first user based, at least in part, on which risk group the first user has been placed, wherein the injury recovery and/or injury prevention plan comprises a physical recovery component and a psychosocial health component that is tailored to the risk group into which the first user has been placed, wherein the plan is accessible to the first user via a first portal provided on a cloud-based platform.

2. The system of claim 1, wherein the psychosocial component of the injury recovery and/or injury prevention plan comprises transmission of one or more communication messages to the first user.

3. The system of claim 2, wherein the risk groups comprise a first risk group associated with a low level of guidance and care provider involvement, a second risk group associated with a medium level of guidance and care provider involvement greater than the low level, and a third risk group associated with a high level of guidance and care provider involvement greater than the medium level.

4. The system of claim 3, wherein the computer server is configured to transmit the one or more communication messages to the first user based, at least in part, on the level of guidance and care provider involvement associated with the risk group in which the first user has been placed.

5. The system of claim 4, wherein:
at the low level of guidance and care provider involvement, the communication messages comprise automated, chatbot-based communications;
at the medium level of guidance and care provider involvement, the communication messages comprise a combination of automated, chatbot-based communications and human-based communications; and
at the high level of guidance and care provider involvement, the communication messages comprise human-based communications.

6. The system of claim 1, wherein tailoring of the injury recovery and/or injury prevention plan to the first user comprises automatically predicting, based on real-time analysis of the first user data and risk group data, a level of care to be associated with the plan and types of content to be provided to the first user as part of the physical recovery and psychosocial health components of the plan.

7. The system of claim 6, wherein the first user data comprises at least one of injury data, personal data associated with the first user, and preference data associated with the first user's preferred level of guidance for injury recovery and/or injury prevention.

8. The system of claim 7, wherein the injury data comprises information associated with the injury, the information selected from the group consisting of: location of the injury on the first user's body; symptoms of injury; self-reported pain scale value associated with injury; limitations in function associated with injury; date of injury occurrence; and activity performed by first user at the time of injury occurrence.

9. The system of claim 7, wherein the personal data comprises traits and characteristics of the first user selected from the group consisting of: name; date of birth, height, weight, gender, medical history, comorbidity, and smoking status.

10. The system of claim 7, wherein the preference data comprises at least one of a self-reported preferred level of guidance and/or care provider involvement related the injury recovery and/or injury prevention plan and self-reported level of experience with injury recovery and/or injury prevention.

11. The system of claim 1, wherein the physical recovery and psychosocial health components of the injury recovery and/or injury prevention plan are selected from the group consisting of: one or more suggested consultations with a care provider; one or more suggested injury recovery and/or injury prevention treatments; and one or more communication messages to be transmitted to the first user.

12. The system of claim 11, wherein the one or more suggested injury recovery and/or injury prevention treatments comprise physical exercises.

13. The system of claim 11, wherein the one more communication messages comprise questions concerning at least one of the first user's current physical health status, the first user's current psychosocial health status, and the first user's participation with the injury recovery and/or injury prevention plan.

14. The system of claim 11, wherein the computer server is configured to monitor the first user's participation and engagement with the injury recovery and/or injury prevention plan based, at least in part, on the first user's interaction with at least one of the physical recovery and psychosocial health components.

15. The system of claim 14, wherein the computer server is configured to receive at least one of:
feedback indicating whether the first user has attended the one or more suggested consultations with the care provider and/or whether the first user has started and/or completed the one or more suggested injury recovery and/or injury prevention treatments; and
one or more responses from the first user to one or more communication messages transmitted to the first user.

16. The system of claim 15, wherein, based on real-time analysis of the first user's feedback and/or the one or more responses from the first user, the computer server is configured to adjust the injury recovery and/or injury prevention plan.

17. The system of claim 16, wherein adjustments to the injury recovery and/or injury prevention plan comprise one or more adjustments to the physical recovery component and/or psychosocial component selected from the group consisting of: adjusting frequency of the one or more initially suggested consultations with a care provider; updating the plan to include one or more additional suggested consultations with one or more additional care providers; updating the plan to include one or more additional suggested injury recovery and/or injury prevention treatments; updating the plan to remove the one or more initially suggested injury recovery and/or injury prevention treatments; adjusting frequency of the one or more communication messages to be transmitted to the first user; and adjusting content of the one or more communication messages to be transmitted to the first user.

18. The system of claim 16, wherein, based on real-time analysis of the first user's feedback and/or the one or more responses from the first user, the computer server is configured to re-stratify the first user into one of the plurality of risk groups.

19. The system of claim 14, wherein the computer server is configured to track participation and engagement data related to the first user's participation and engagement with the injury recovery and/or injury prevention plan, wherein tracking participation and engagement data comprises aggregating and storing the participation and engagement data in a database.

20. The system of claim 19, wherein the participation and engagement data is accessible to at least the first user via a first portal provided on the cloud-based platform and further accessible to at least an authorized second user via a second portal provided on the cloud-based platform.

* * * * *